United States Patent
Fujimoto et al.

(10) Patent No.: US 7,354,510 B2
(45) Date of Patent: Apr. 8, 2008

(54) EXTRACTING APPARATUS

(75) Inventors: Keiichi Fujimoto, Minamiashigara (JP); Nobuyuki Torisawa, Minamiashigara (JP)

(73) Assignee: Fujifilm Corporation, Tokyo (JP)

( * ) Notice: Subject to any disclaimer, the term of this patent is extended or adjusted under 35 U.S.C. 154(b) by 519 days.

(21) Appl. No.: 10/920,440

(22) Filed: Aug. 18, 2004

(65) Prior Publication Data
US 2005/0045533 A1    Mar. 3, 2005

(30) Foreign Application Priority Data
Aug. 19, 2003  (JP) .............................. 2003-295086
Sep. 19, 2003  (JP) .............................. 2003-328252

(51) Int. Cl.
*B01D 17/12* (2006.01)
*G01N 30/00* (2006.01)

(52) U.S. Cl. .................... 210/90; 210/97; 210/141; 210/340; 422/69; 422/101; 422/103; 422/104; 422/112; 73/863.01

(58) Field of Classification Search .................. 210/90, 210/97, 141, 143, 741, 340; 422/69–71, 422/99–104, 105, 112, 113; 73/863.01, 863.02, 73/863.21; 436/177, 178, 86
See application file for complete search history.

(56) References Cited

U.S. PATENT DOCUMENTS

| | | | |
|---|---|---|---|
| 5,114,858 A | 5/1992 | Williams et al. | |
| 5,645,723 A | 7/1997 | Fujishiro et al. | |
| 5,844,147 A * | 12/1998 | Fiedler et al. | 73/863.21 |
| 6,136,555 A | 10/2000 | Jones | |
| 6,881,579 B2 * | 4/2005 | Hilson et al. | 436/47 |
| 2001/0020603 A1 * | 9/2001 | Moorehead et al. | 210/741 |
| 2003/0170664 A1 | 9/2003 | Mori et al. | |
| 2004/0189311 A1 * | 9/2004 | Glezer et al. | 324/444 |

* cited by examiner

*Primary Examiner*—Joseph Drodge
(74) *Attorney, Agent, or Firm*—Sughrue Mion, PLLC

(57) ABSTRACT

A mechanism for introducing pressurized air into an extracting cartridge comprises an air pump, an on-off valve, and a pressure sensor for detecting an internal pressure within the extracting cartridge. The on-off valve is turned on in order to introduce the pressurized air into the extracting cartridge. When the internal pressure detected by the pressure sensor has become equal to a predetermined pressure range for a pressurization upper limit, the on-off valve is turned off in order to confine the area within the extracting cartridge in the pressurized state, the pressure being thereby exerted upon a sample liquid, a washing liquid, or a recovery liquid having been injected into the extracting cartridge.

15 Claims, 10 Drawing Sheets

EXTRACTING APPARATUS

BACKGROUND OF THE INVENTION

1. Field of the Invention

This invention relates to an extracting apparatus for extracting a predetermined substance such as a nucleic acid from a sample liquid by use of at least one extracting cartridge provided with a filter member. This invention particularly relates to extraction of the predetermined substance through pressurization of an area within at least one extracting cartridge with pressurized air introduced into the extracting cartridge.

2. Description of the Related Art

As extracting methods, for example in techniques for extracting a nucleic acid, a centrifugal technique, a technique utilizing magnetic beads, a technique utilizing a filter, and the like, have heretofore been known.

For example, there has been proposed a nucleic acid extracting apparatus utilizing filters. With the proposed nucleic acid extracting apparatus, a plurality of filter tubes, each of which accommodates a filter therein, are set on a rack, and sample liquids are respectively injected into the filter tubes. Also, a region around a bottom of the rack is closed with an air chamber via a sealing material, and a pressure within the air chamber is reduced. Areas within all of the filter tubes are thus simultaneously subjected to suction from discharging sides of the filter tubes, and the sample liquids contained in the filter tubes are thus caused to pass through the filters of the filter tubes. Nucleic acids contained in the sample liquids are thus adsorbed to the filters of the filter tubes. Thereafter, a washing liquid and an eluting liquid are successively injected into the filter tubes and subjected to suction at a reduced pressure. The nucleic acids having been adsorbed to the filters of the filter tubes are thus washed with the washing liquid and eluted from the filters. (The aforesaid nucleic acid extracting apparatus utilizing filters is described in, for example, U.S. Pat. No. 5,645,723.)

As described above, a separation purification method of a nucleic acid, comprising the step of using a predetermined filter for separating and recovering the sample liquid after the nucleic acid contained in the sample liquid is adsorbed to the filter, is disclosed in U.S. Patent Laid-Open No. 20030170664. Further, a method for extracting by injecting the sample liquid into the separation purification unit including the filter and pressurizing the sample liquid is adopted.

However, the conventional nucleic acid extracting apparatus described above has the problems in that, in cases where the nucleic acid extracting apparatus has a large size so as to be appropriate for analyses of large amounts of samples and in cases where the number of the samples is small, and the frequency of analyses is low, the cost of the nucleic acid extracting apparatus is not capable of being kept low, and the processing efficiency is not capable of being kept high.

Also, as for nucleic acid extracting apparatuses, it is desired that the processing is capable of being performed quickly and efficiently without any contamination occurring, and that the sizes of the nucleic acid extracting apparatuses are capable of being kept small. However, the problems described below occur with the nucleic acid extracting apparatus proposed in U.S. Pat. No. 5,645,723.

Specifically, with a nucleic acid extracting apparatus, in which the areas within all of the filter tubes are simultaneously subjected to suction as in the cases of the nucleic acid extracting apparatus proposed in U.S. Pat. No. 5,645,723, in cases where the sample liquids have different characteristics as in the cases of sampled whole blood, at the time at which the suction with respect to a certain filter tube is completed, and the resistance against the suction with respect to the certain filter tube disappears, the effect of the reduced pressure acting upon the other filter tubes becomes small. As a result, the problems often occur in that the processing on sample liquids having a comparatively high viscosity is not capable of being completed. In cases where the capacity of the reduced pressure is increased in order to prevent the aforesaid problems from occurring, the size of the extracting apparatus is not capable of being kept small. Also, due to a large volume of the reduced pressure, a long time is required to obtain the reduced pressure. Further, it is not always possible to detect the completion of the discharging of all of the sample liquids. Therefore, the setting time is not capable of being kept short, and the processing efficiency is not capable of being enhanced. Furthermore, the problems occur in that a sample liquid having a low viscosity is vigorously discharged from the filter tube, and a bubble-like splash of the sample liquid clings to an adjacent filter tube and an adjacent area of the rack and causes contamination to occur. As a result, the accuracy of the analysis is not capable of being kept high.

In particular, with the extracting apparatus, in which the areas within all of the filter tubes are simultaneously subjected to vacuum suction, the problems occur in that, in cases where air resistance does not occur in one of the filter tubes due to a sample liquid injection failure, a filter tube loading failure, or the like, a normal operation is not capable of being performed. Also, it is not always possible to constitute a mechanism for performing independent sucking operation for each of the plurality of the filter tubes.

A method for recovering the liquid by adsorbing the nucleic acid to the filter by pressurization is disclosed in U.S. Patent Laid-Open No. 20030170664. However, a specific extracting apparatus is not disclosed. In the extracting apparatus which adopts the pressurization method, problems will arise in its pressurization control method. Problems will also arise in contamination due to scattering of the discharged liquid during pressurization, reliability in sealing, or the like.

SUMMARY OF THE INVENTION

The primary object of the present invention is to provide an extracting apparatus, which is capable of automatically performing quick and efficient extraction of a nucleic acid from a sample liquid and is capable of performing the extraction of the nucleic acid through optimum supply of pressurized air in accordance with the kind of the sample liquid.

Another object of the present invention is to provide an extracting apparatus, which is capable of being kept small in size, and in which problems with regard to contamination are capable of being prevented from occurring, and extraction accuracy is capable of being kept high.

The present invention provides an extracting apparatus for performing an extracting operation by use of at least one extracting cartridge provided with a filter member, the extracting operation comprising:

injecting a sample liquid, which contains a predetermined substance, into the extracting cartridge, the sample liquid being thereby caused to pass through the filter member of the extracting cartridge under pressure, the predetermined substance contained in the sample liquid being thus adsorbed to the filter member of the extracting cartridge, the apparatus comprising:

a pressurized air introducing means for introducing pressurized air into the at least one extracting cartridge, including:

a) an air pump, b) at least one on-off valve for turning on and off the introduction of the pressurized air into the at least one extracting cartridge, and c) at least one pressure sensor for detecting an internal pressure within the at least one extracting cartridge, the pressurized air introducing means operating such that:

the at least one on-off valve is turned on in order to introduce the pressurized air into the at least one extracting cartridge, and at the time at which the internal pressure detected by the at least one pressure sensor for the at least one extracting cartridge has become equal to a predetermined pressure range for a pressurization upper limit, the at least one on-off valve is turned off in order to confine the area within the at least one extracting cartridge in the pressurized state, the pressure being thereby exerted upon the sample liquid, the washing liquid, or the recovery liquid having been injected into the at least one extracting cartridge.

The extracting apparatus in accordance with the present invention should preferably be modified such that the predetermined pressure range for the pressurization upper limit is altered in accordance with characteristics of the sample liquid.

Also, the extracting apparatus in accordance with the present invention should preferably be modified such that information, which corresponds to the kind of the sample liquid accommodated in the at least one extracting cartridge, is inputted into the extracting apparatus, and an extraction processing procedure and setting values, including the predetermined pressure range for the pressurization upper limit, are altered in accordance with the inputted information.

Further, the extracting apparatus in accordance with the present invention should preferably be modified such that a judgment is made as to whether the internal pressure is within a predetermined pressure range when a predetermined length of time has elapsed after the at least one on-off valve was turned on in order to begin the supply of the pressurized air into the at least one extracting cartridge.

The state, in which the internal pressure is within the predetermined pressure range, as described above, is a state in which the extracting cartridge has not been set in the extracting apparatus, a state in which the sample liquid, the washing liquid, or the recovery liquid has not been injected into the at least one extracting cartridge, or a state in which the area within the at least one extracting cartridge has not been confined appropriately.

Furthermore, the extracting apparatus in accordance with the present invention should preferably be modified such that the at least one on-off valve is turned on in order to introduce the pressurized air into the at least one extracting cartridge, at the time at which the internal pressure detected by the at least one pressure sensor for the at least one extracting cartridge has become equal to the predetermined pressure range for the pressurization upper limit, the at least one on-off valve is turned off in order to confine the area within the at least one extracting cartridge in the pressurized state, the pressure being thereby exerted upon the sample liquid, the washing liquid, or the recovery liquid, which has been injected into the at least one extracting cartridge, the sample liquid, the washing liquid, or the recovery liquid, which has been injected into the at least one extracting cartridge, being thereby caused to pass through the filter member of the at least one extracting cartridge under pressure and discharged from the at least one extracting cartridge, and at the time at which a pressure drop accompanying completion of the liquid discharging from the at least one extracting cartridge is detected, it is judged that the pressurization has been completed.

The judgment of the completion of the pressurization may be made by directly detecting the pressure drop at the time of the completion of the liquid discharging from the at least one extracting cartridge. Alternatively, the judgment of the completion of the pressurization may be made by detecting that the quantity of the variation in pressure drop per unit time has become equal to at least a predetermined value. As another alternative, the judgment of the completion of the pressurization may be made by detecting that the detected pressure has become equal to at most a predetermined pressure range for the pressurization completion judgment.

Also, the extracting apparatus in accordance with the present invention should preferably be modified such that a state, in which the internal pressure confined within the at least one extracting cartridge is equal to at least a predetermined pressure range for filter clogging detection when a predetermined length of time has elapsed, is judged as being a state in which filter clogging has occurred.

Further, the extracting apparatus in accordance with the present invention should preferably be modified such that a state, in which the internal pressure confined within the at least one extracting cartridge is higher than a predetermined pressure range and is lower than the predetermined pressure range for the pressurization upper limit for the turning off of the at least one on-off valve, and liquid discharging from the at least one extracting cartridge is completed in this state, is judged as being a liquid quantity deficiency state, in which the liquid injection quantity is smaller than a predetermined value.

The extracting apparatus in accordance with the present invention is capable of performing the extracting operation comprising:

injecting the sample liquid, which contains the predetermined substance, into the extracting cartridge provided with the filter member, and pressurizing the area within the extracting cartridge into which the sample liquid has been injected, the sample liquid being thereby caused to pass through the filter member of the extracting cartridge under pressure, the predetermined substance contained in the sample liquid being thus adsorbed to the filter member of the extracting cartridge.

The extracting apparatus in accordance with the present invention is thus capable of performing efficient extraction of the predetermined substance from the sample liquid and is capable of being kept small in size.

Also, the extracting apparatus in accordance with the present invention comprises the pressurized air introducing means for introducing the pressurized air into the at least one extracting cartridge. The pressurized air introducing means is provided with: (a) the air pump, (b) the at least one on-off valve for turning on and off the introduction of the pressurized air into the at least one extracting cartridge, and (c) the at least one pressure sensor for detecting the internal pressure within the at least one extracting cartridge. The pressurized air introducing means operates such that:

the at least one on-off valve is turned on in order to introduce the pressurized air into the at least one extracting cartridge, and at the time at which the internal pressure detected by the at least one pressure sensor for the at least one extracting cartridge has become equal to the predetermined pressure range for the pressurization upper limit, the at least one on-off valve is turned off in order to confine the area within the at least one extracting cartridge in the pressurized state, the pressure being thereby exerted upon the sample liquid, the washing liquid, or the recovery liquid having been injected into the at least one extracting cartridge.

Therefore, with the extracting apparatus in accordance with the present invention, the introduction of the pressurized air into the extracting cartridge is capable of being performed reliably. Also, since the initial pressurization state is set at a predetermined state, the reliability of the extraction processing is capable of being enhanced.

With the extracting apparatus in accordance with the present invention, wherein the predetermined pressure range for the pressurization upper limit is altered in accordance with the characteristics of the sample liquid, the supply of the pressurized air is capable of being performed with a pressure optimum for the kind of the sample liquid. Therefore, the processing for extracting the nucleic acid is capable of being performed reliably, such that the problems with regard to contamination may not occur, and such that the processing efficiency may be kept high.

Also, the extracting apparatus in accordance with the present invention may be modified such that the information, which corresponds to the kind of the sample liquid accommodated in the at least one extracting cartridge, is inputted into the extracting apparatus, and the extraction processing procedure and the setting values, including the predetermined pressure range for the pressurization upper limit, are altered in accordance with the inputted information. With the modification described above, an optimum pressure, an optimum pressurization time, and the like, are capable of being set in accordance with the alteration in characteristics of the sample liquid. Therefore, the extraction processing free from contamination is capable of being performed efficiently.

Further, the extracting apparatus in accordance with the present invention may be modified such that a judgment is made as to whether the internal pressure of the extracting cartridge is within the predetermined pressure range when the predetermined length of time has elapsed after the at least one on-off valve was turned on in order to begin the supply of the pressurized air into the at least one extracting cartridge. With the modification described above, it is possible to detect the state in which the extracting cartridge has not been set in the extracting apparatus, the state in which the sample liquid, the washing liquid, or the recovery liquid has not been injected into the at least one extracting cartridge, or the state in which the area within the at least one extracting cartridge has not been confined appropriately. Therefore, malfunction of the extracting apparatus due to an operation mistake made by the operator, a stoppage of mechanisms of the extracting apparatus, and the like, are capable of being avoided. Accordingly, the extraction processing is capable of being performed reliably in the normal operating state.

Furthermore, the extracting apparatus in accordance with the present invention may be modified such that the at least one on-off valve is turned on in order to introduce the pressurized air into the at least one extracting cartridge, at the time at which the internal pressure detected by the at least one pressure sensor for the at least one extracting cartridge has become equal to the predetermined pressure range for the pressurization upper limit, the at least one on-off valve is turned off in order to confine the area within the at least one extracting cartridge in the pressurized state, the pressure being thereby exerted upon the sample liquid, the washing liquid, or the recovery liquid, which has been injected into the at least one extracting cartridge, the sample liquid, the washing liquid, or the recovery liquid, which has been injected into the at least one extracting cartridge, being thereby caused to pass through the filter member of the at least one extracting cartridge under pressure and discharged from the at least one extracting cartridge, and at the time at which the pressure drop accompanying completion of the liquid discharging from the at least one extracting cartridge is detected, it is judged that the pressurization has been completed.

With the modification described above, in cases where the liquid discharging time varies due to alteration in viscosity of the sample liquid, or the like, the completion of the pressurization in each of extracting cartridges is capable of being judged accurately. Therefore, the automatic extraction processing is capable of being performed with a high efficiency.

Also, the extracting apparatus in accordance with the present invention maybe modified such that the state, in which the internal pressure confined within the at least one extracting cartridge is equal to at least the predetermined pressure range for the filter clogging detection when the predetermined length of time has elapsed, is judged as being the state in which filter clogging has occurred. With the modification described above, the filter clogging is capable of being detected easily and reliably, and necessary control is capable of being performed.

Further, the extracting apparatus in accordance with the present invention may be modified such that the state, in which the internal pressure confined within the at least one extracting cartridge is higher than the predetermined pressure range and is lower than the predetermined pressure range for the pressurization upper limit for the turning off of the at least one on-off valve, and liquid discharging from the at least one extracting cartridge is completed in this state, is judged as being the liquid quantity deficiency state, in which the liquid injection quantity is smaller than the predetermined value. With the modification described above, a shortage of the sample liquid introduced into the extracting cartridge due to an erroneous operation of the operator or a shortage of the quantity of the washing liquid or the recovery liquid due to malfunction of a liquid injecting mechanism is capable of being detected, and the reliability of the extraction processing is capable of being enhanced.

DESCRIPTION OF THE PREFERRED EMBODIMENTS

The present invention will hereinbelow be described in further detail with reference to the accompanying drawings.

Figure 1:
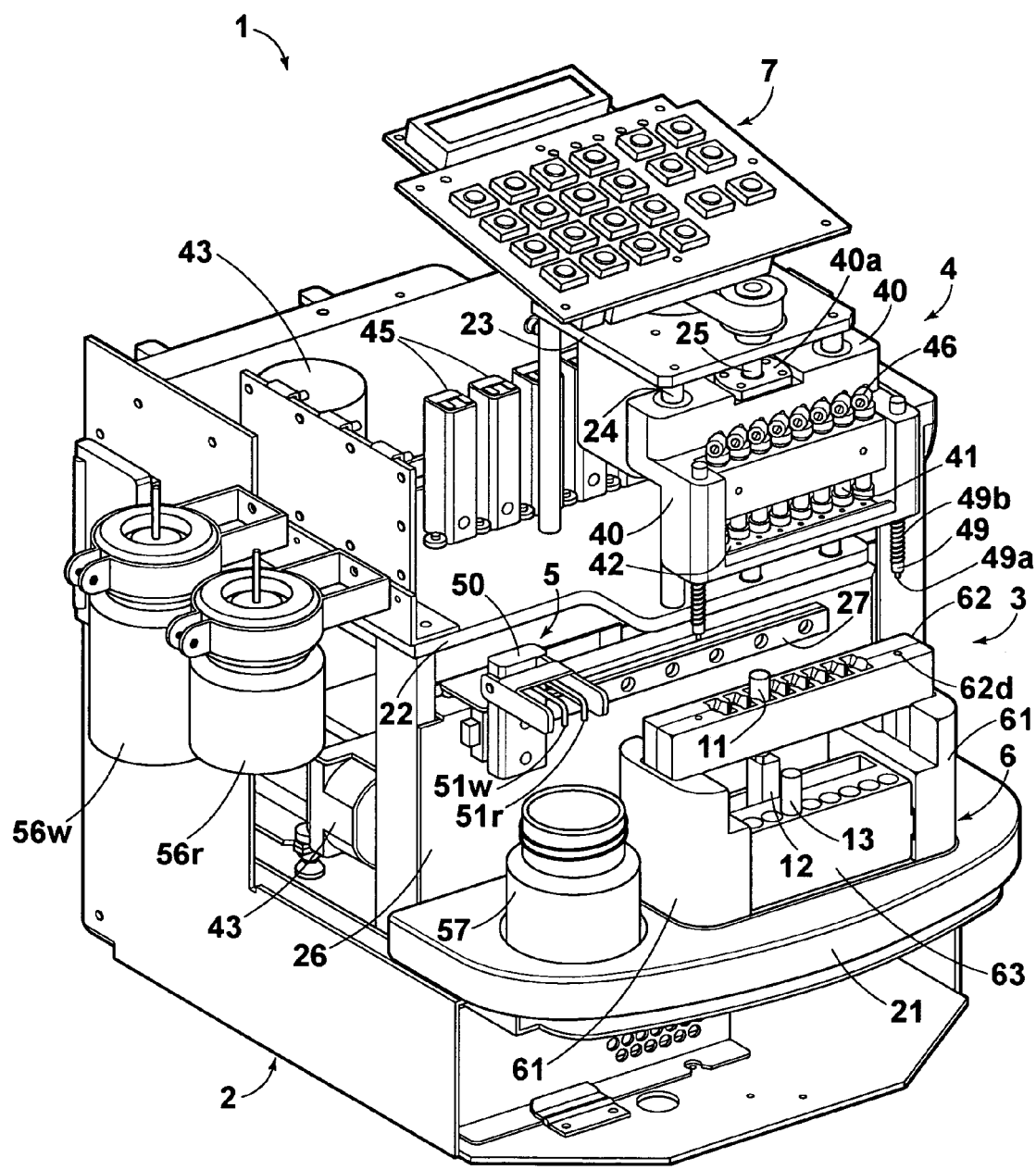
FIG. 1 is a perspective view showing an embodiment of the nucleic acid extracting apparatus in accordance with the present invention with a cover being removed.
Figure 2:
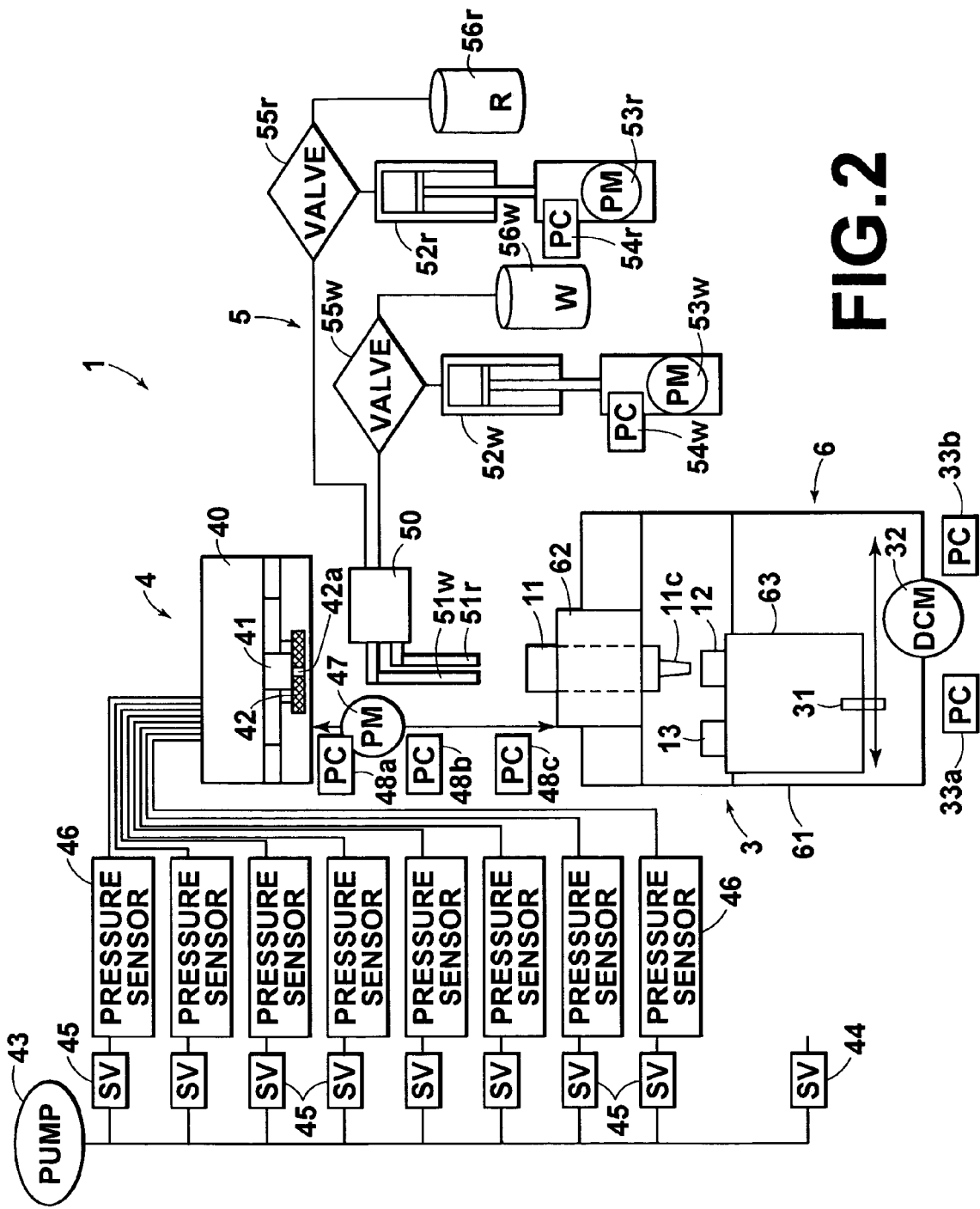
FIG. 2 is a block diagram showing mechanisms of the nucleic acid extracting apparatus of FIG. 1.
Figure 3:
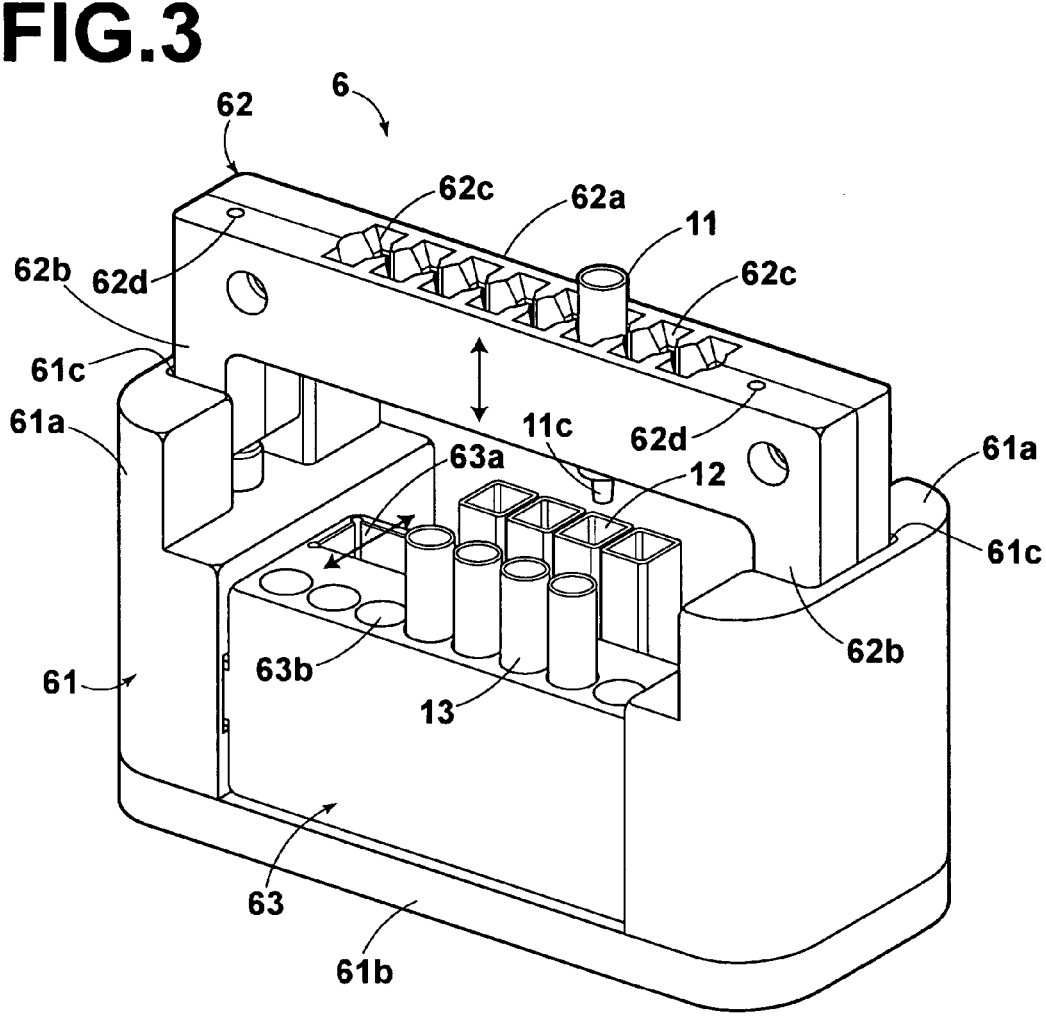
FIG. 3 is a perspective view showing a rack of a loading mechanism.
Figure 4:
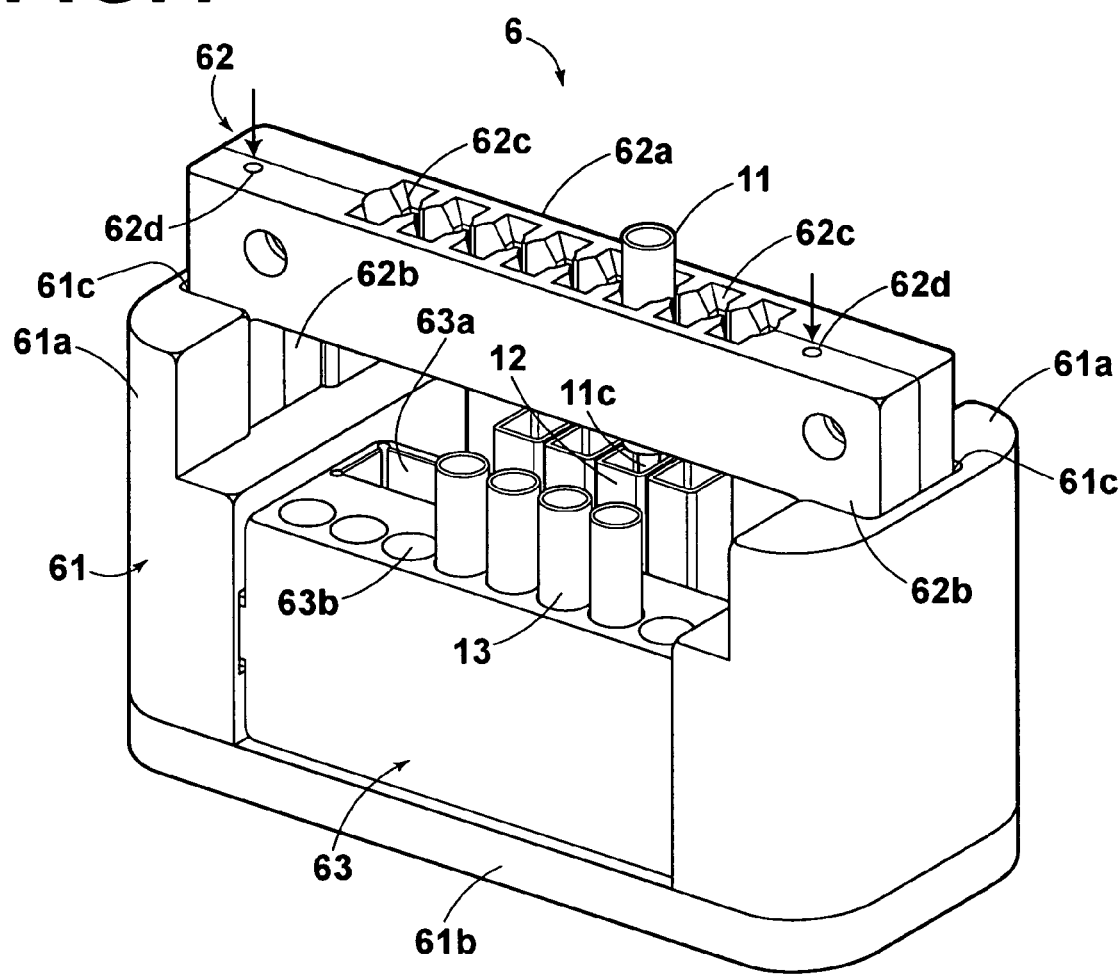
FIG. 4 is a perspective view showing the rack of FIG. 3 in the state in which the rack is being used.
Figure 5:
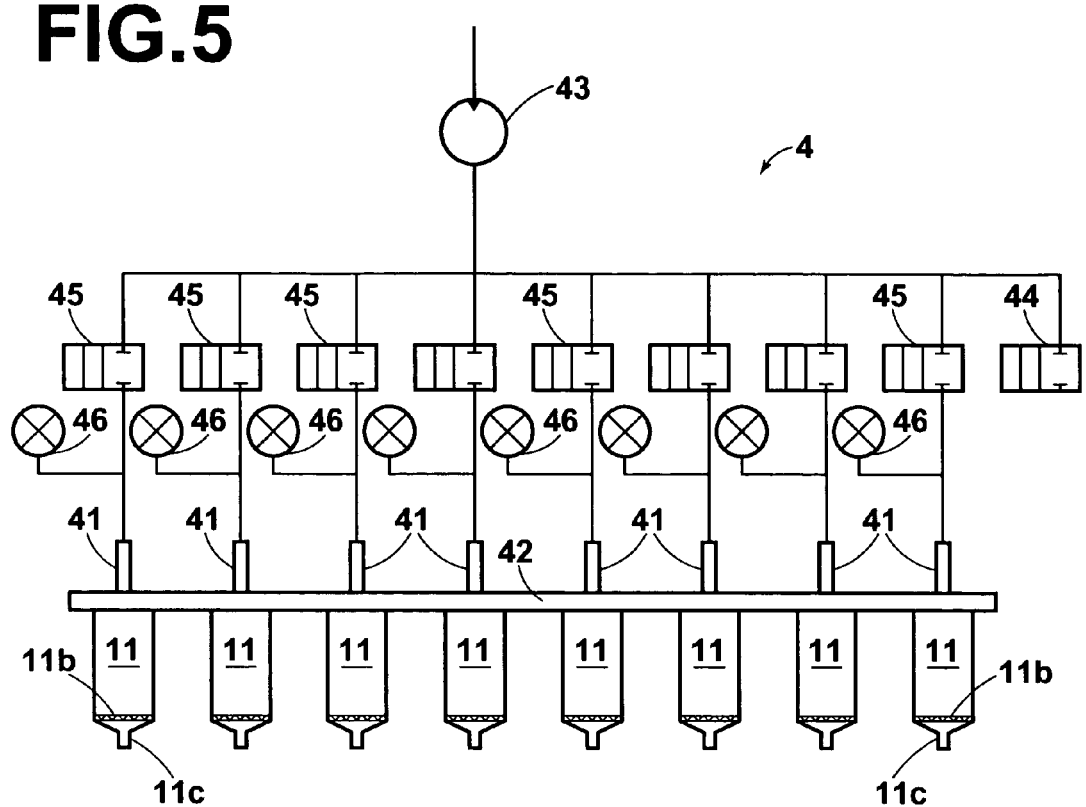
FIG. 5 is an explanatory view showing an air system of a pressurized air supplying mechanism.
Figure 6:
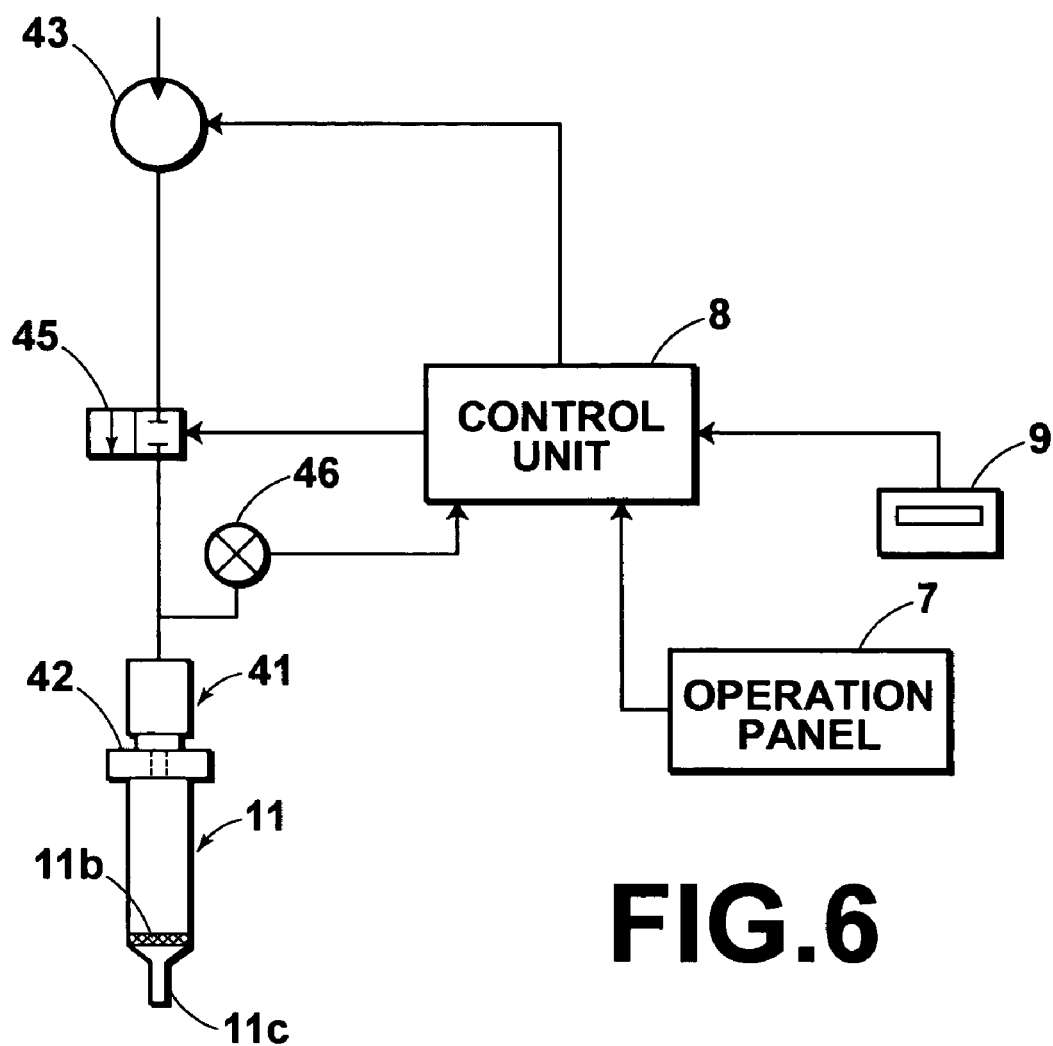
FIG. 6 is an explanatory view showing a control system of the pressurized air supplying mechanism.
Figure 7:
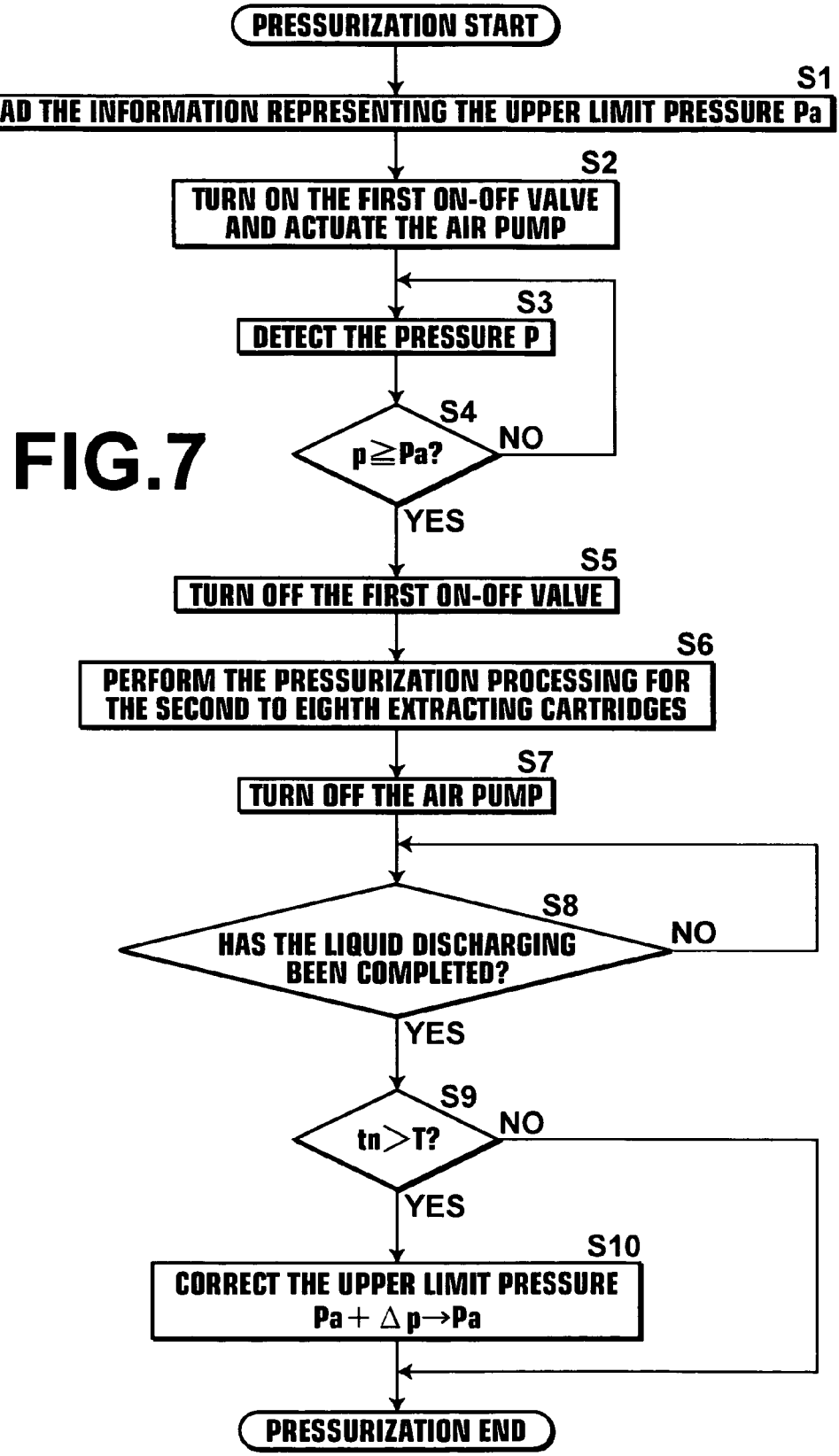
FIG. 7 is a flow chart showing an example of control of pressurization.
Figure 8:
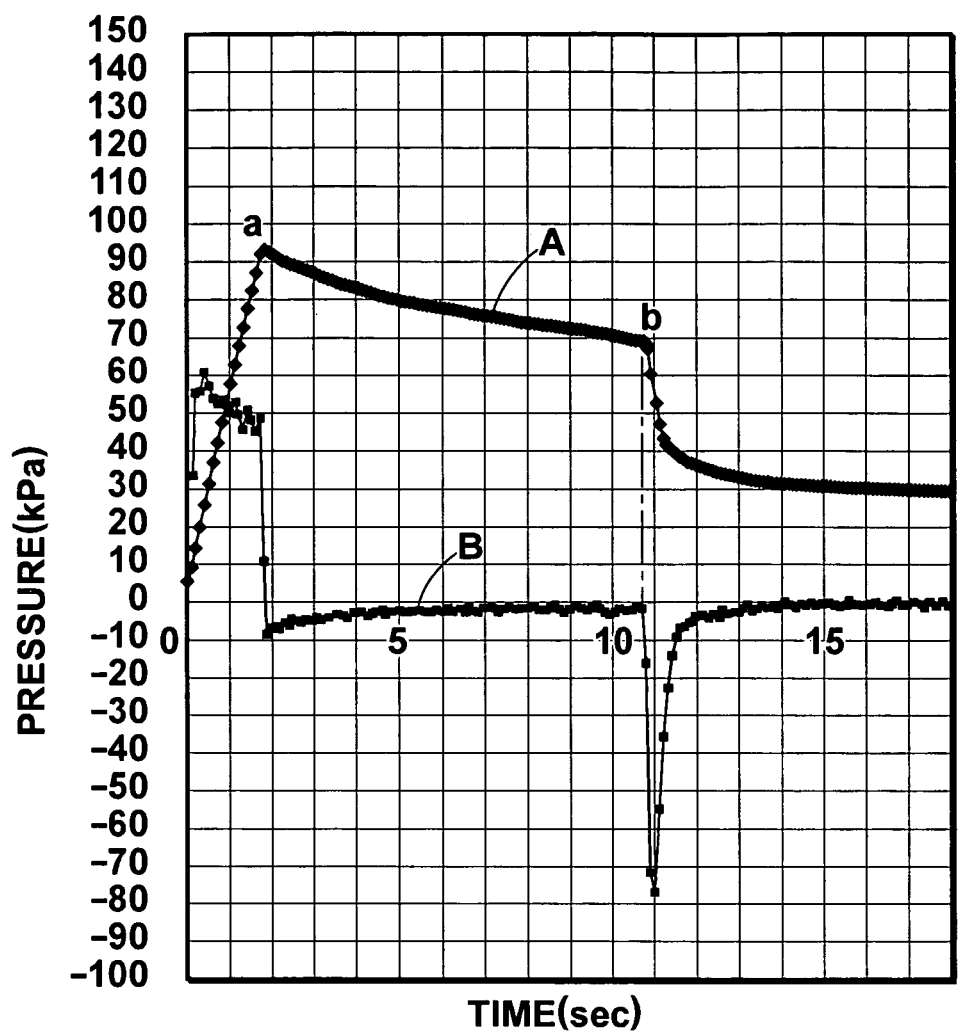
FIG. 8 is a graph showing variation in internal pressure within an extracting cartridge.

FIG. 1 is a perspective view showing an embodiment of the extracting apparatus in accordance with the present invention with a cover being removed. FIG. 2 is a block diagram showing mechanisms of the nucleic acid extracting apparatus of FIG. 1. FIG. 3 is a perspective view showing a rack of a loading mechanism. FIG. 4 is a perspective view showing the rack of FIG. 3 in the state in which the rack is being used. FIG. 5 is an explanatory view showing an air system of a pressurized air supplying mechanism. FIG. 6 is an explanatory view showing a control system of the pressurized air supplying mechanism. FIG. 7 is a flow chart showing an example of control of pressurization. FIG. 8 is a graph showing variation in internal pressure within an extracting cartridge. FIGS. 9A to 9G are flow diagrams showing an extracting operation. FIG. 10 is a perspective view showing an extracting cartridge.

A nucleic acid extracting apparatus 1 illustrated in FIG. 1 extracts a nucleic acid from a sample liquid by use of an extracting cartridge (a filter cartridge) 11 illustrated in FIG. 10. As illustrated in FIG. 10, the extracting cartridge 11 comprises a tubular main body 11a having an opening at its top end. The extracting cartridge 11 also comprises a filter member 11b, which is held within the tubular main body 11a and at a bottom of the tubular main body 11a. Part of the tubular main body 11a, which part is lower than the filter member 11b, is formed in a funnel-like shape. Also, a discharging bottom end 11c, which has a nozzle-like shape having a reduced diameter, protrudes by a predetermined length from a center region of the bottom of the funnel-like part of the tubular main body 11a. Further, vertically extending protrusions 11d, 11d are formed on opposite sides of a side wall of the tubular main body 11a. As will be described later, a sample liquid, a washing liquid, or a recovery liquid is injected through the top opening of the tubular main body 11a into the extracting cartridge 11. Also, pressurized air is introduced through the top opening of the tubular main body 11a into the extracting cartridge 11 in order to cause the sample liquid, the washing liquid, or the recovery liquid to pass through the filter member 11b and to discharge the liquid through the discharging bottom end 11c into one of waste liquid vessels 12, 12, . . . or recovery vessels 13, 13, . . . , which will be described later. In the example of FIG. 10, the tubular main body 11a comprises an upper half and a lower half, which are fitted to each other.

Basically, the nucleic acid extracting apparatus 1 performs the extraction of the nucleic acid with the extracting steps illustrated in FIGS. 9A to 9G. Specifically, firstly, in the step illustrated in FIG. 9A, a sample liquid S containing the nucleic acid, which sample liquid S has been subjected to dissolution processing, is injected into the extracting cartridge 11, which is located above the corresponding waste liquid vessel 12. Thereafter, in the step illustrated in FIG. 9B, the pressurized air is introduced into the extracting cartridge 11, and the area within the extracting cartridge 11 is thus pressurized. As a result, the sample liquid S is caused to pass through the filter member 11b of the extracting cartridge 11 under pressure, and the nucleic acid contained in the sample liquid S is adsorbed to the filter member 11b. The liquid having passed through the filter member 11b is discharged into the corresponding waste liquid vessel 12.

Figure 9:
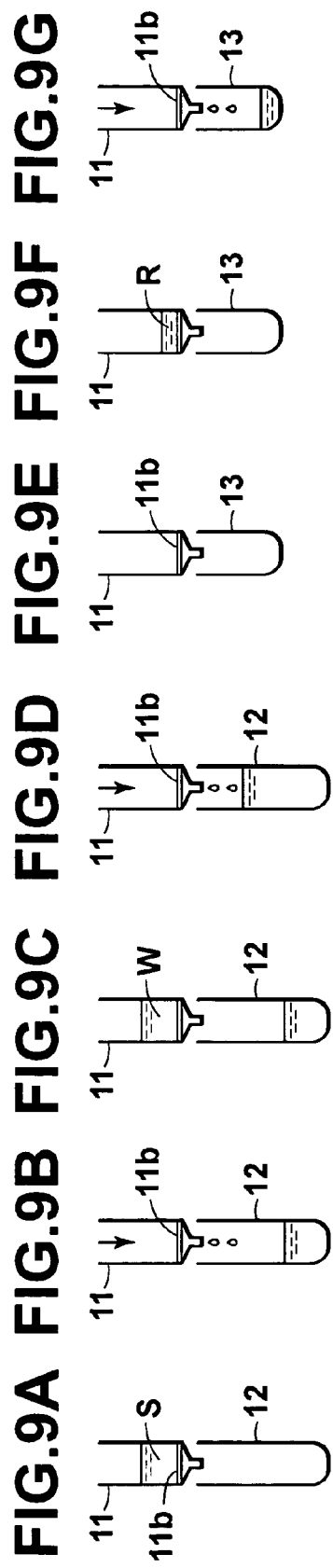
FIGS. 9A to 9G are flow diagrams showing an extracting operation.
Figure 10:
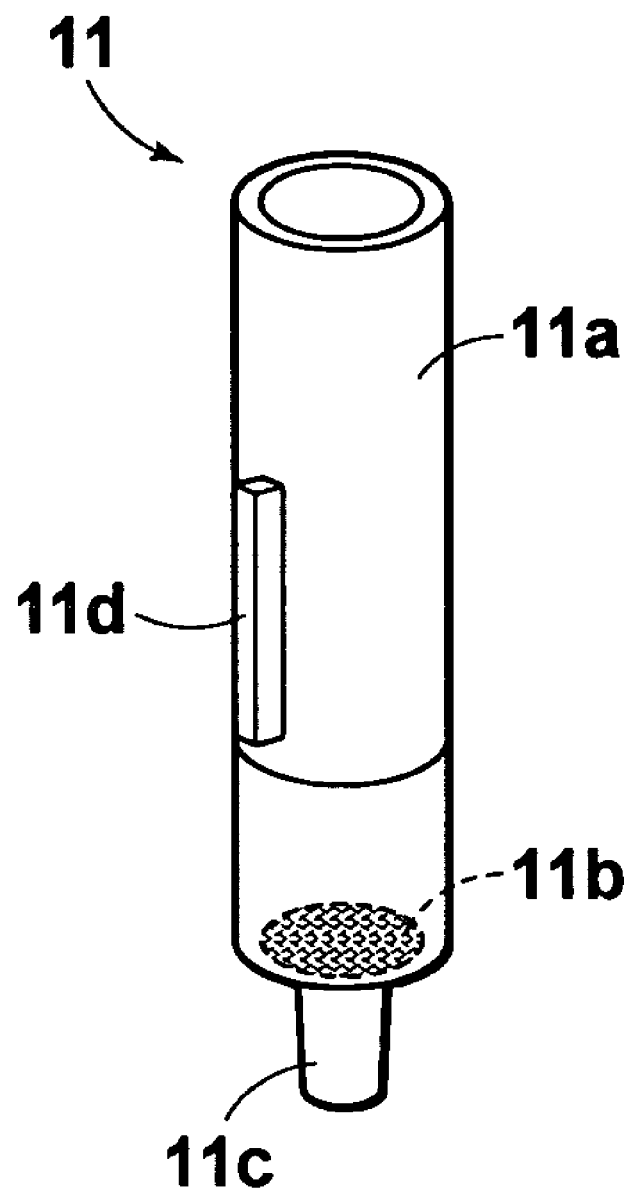
FIG. 10 is a perspective view showing an extracting cartridge.

Thereafter, in the step illustrated in FIG. 9C, a washing liquid W is automatically injected into the extracting cartridge 11. Also, in the step illustrated in FIG. 9D, the pressurized air is introduced into the extracting cartridge 11, and the area within the extracting cartridge 11 is thus pressurized. As a result, the washing liquid W is caused to pass through the filter member 11b of the extracting cartridge 11 under pressure. In this manner, impurities are removed by the washing liquid W from the extracting cartridge 11, while the nucleic acid is being kept in the state in which the nucleic acid has been adsorbed to the filter member 11b. The washing liquid W having passed through the filter member 11b is discharged into the waste liquid vessel 12. The step illustrated in FIG. 9C and the step illustrated in FIG. 9D may be iterated a plurality of times.

Thereafter, in the step illustrated in FIG. 9E, the waste liquid vessel 12, which is located under the extracting cartridge 11, is replaced by the recovery vessel 13. Also, in the step illustrated in FIG. 9F, a recovery liquid R is automatically injected into the extracting cartridge 11. Thereafter, in the step illustrated in FIG. 9G, the pressurized air is introduced into the extracting cartridge 11, and the area within the extracting cartridge 11 is thus pressurized. As a result, the recovery liquid R is caused to pass through the filter member 11b of the extracting cartridge 11 under pressure. In this manner, the binding force between the filter member 11b and the nucleic acid is weakened. The nucleic acid having been adsorbed to the filter member 11b of the extracting cartridge 11 is thus separated by the recovery liquid R from the filter member 11b. The recovery liquid R, which now contains the nucleic acid, is discharged from the extracting cartridge 11 and recovered into the recovery vessel 13. The filter member 11b of the extracting cartridge 11 has a porosity such that the nucleic acid is basically capable of passing through the pores. The surface of the filter member 11b has characteristics of adsorbing the nucleic acid, which is contained in the sample liquid, with chemical binding force. The filter member 11b is constituted such that the filter member 11b keeps the adsorption of the nucleic acid during the washing with the washing liquid, and such that the filter member 11b reduces the force of adsorption of the nucleic acid and releases the nucleic acid during the recovery of the nucleic acid with the recovery liquid. Specifically, by way of example, as described in, for example, U.S. patent Laid-Open No. 20030170664, the filter member 11b may be constituted of an organic high-molecular weight material having a hydroxyl group on a surface. The organic high-molecular weight material having the hydroxyl group on the surface should preferably be a surface saponification product of an acetylcellulose. The acetylcellulose may be monoacetylcellulose, diacetylcellulose, or triacetylcellulose. Among the above-enumerated acetylcelluloses, the triacetylcellulose is particularly preferable. The surface of the surface saponification product of the acetylcellulose has been saponified by contact with a saponification processing liquid (e.g., NaOH), and the structure body of the surface saponification product of the acetylcellulose is constituted of the acetylcellulose. In such cases, the quantity (the density) of the hydroxyl group in the surface is capable of being adjusted with the degree of the surface saponification processing (i.e., the surface saponification degree). In order for the effect of adsorbing the nucleic acid to be enhanced, the quantity of the hydroxyl group should preferably be as large as possible. For example, in the cases of the acetylcellulose, such as the triacetylcellulose, the surface saponification degree should preferably be at least approximately 5%, and should more preferably be at least approximately 10%. The acetylcellulose should preferably take on the form of a porous film.

The aforesaid sample liquid S containing the nucleic acid is prepared with a process, wherein a liquid in which the nucleic acid has been dispersed is prepared with the dissolution processing of a sample, which contains a cell or a virus, and a water-soluble organic solvent is added to the liquid in which the nucleic acid has been dispersed. For example, in the cases of diagnostic fields, the sample liquid S containing the nucleic acid may be a liquid having been prepared from an organism material, such as a humor having been taken as a sample (e.g., whole blood, blood plasma, blood serum, urine, feces, semen, or saliva); a plant (or part of a plant); an animal (or part of an animal). Also, the sample liquid S containing the nucleic acid may be a liquid having been prepared from a dissolution product or a homogenate of one of the above-enumerated organism materials. With the dissolution processing, a sample is processed with an aqueous solution containing a reagent for dissolving a cell membrane and a nuclear membrane and solubilizing the nucleic acid. (The reagent is a solution containing, for example, a guanidine salt, a surface active agent, and a proteolytic enzyme.) For example, in cases where the sample is whole blood, red blood corpuscles and various proteins are decomposed and converted into low-molecular weight substances in order for nonspecific adsorption to the filter member $11b$ and clogging of the filter member $11b$ to be prevented from occurring, and dissolution of white blood corpuscles and a nuclear membrane is performed such that the nucleic acid to be extracted may be solubilized. Examples of the water-soluble organic solvents include ethanol, isopropanol, and propanol. Among the above-enumerated water-soluble organic solvents, ethanol is preferable. The concentration of the water-soluble organic solvent should preferably fall within the range of 5% by weight to 90% by weight, and should more preferably fall within the range of 20% by weight to 60% by weight. The concentration of ethanol added should particularly preferably be as high as possible, provided that an agglomerate does not occur.

The washing liquid W has the functions of washing off impurities contained in the sample liquid, which impurities have clung to the filter member $11b$ together with the nucleic acid. The washing liquid W has a composition such that the washing liquid W does not cause the nucleic acid to be separated from the filter member $11b$ and causes the impurities to be separated from the filter member $11b$. The washing liquid W is constituted of a solution containing a principal agent and a buffer agent. When necessary, the solution constituting the washing liquid W may also contain a surface active agent. Examples of the principal agents include aqueous solutions of methanol, ethanol, isopropanol, n-isopropanol, butanol, and acetone. The concentration of the aqueous solution acting as the principal agent may fall within the range of approximately 10% by weight to approximately 100% by weight. The concentration of the aqueous solution acting as the principal agent should preferably fall within the range of approximately 20% by weight to approximately 100% by weight, and should more preferably fall within the range of approximately 40% by weight to approximately 80% by weight.

The recovery liquid R should preferably have a low salt concentration. In particular, the recovery liquid R should preferably be constituted of a solution having a salt concentration of at most 0.5M. For example, purified distilled water, a TE buffer, or the like, may be used as the recovery liquid R.

As illustrated in FIG. 1 and FIG. 2, the nucleic acid extracting apparatus 1 comprises a loading mechanism 3, a pressurized air supplying mechanism 4, and a liquid injecting mechanism 5, which are located on an apparatus main body 2. The loading mechanism 3 holds a plurality of extracting cartridges 11, 11, . . . , the plurality of the waste liquid vessels 12, 12, . . . , and the plurality of the recovery vessels 13, 13, . . . The pressurized air supplying mechanism 4 introduces the pressurized air into each of the extracting cartridges 11, 11, . . . The liquid injecting mechanism 5 injects the washing liquid W into each of the extracting cartridges 11, 11, . . . The liquid injecting mechanism 5 also injects the recovery liquid R into each of the extracting cartridges 11, 11, . . . The loading mechanism 3, the pressurized air supplying mechanism 4, and the liquid injecting mechanism 5 will hereinbelow be described in more detail.

<Loading Mechanism>

The loading mechanism 3 comprises a loading base 21, which is located on a front lower part of the apparatus main body 2. A rack 6, which holds the plurality of the extracting cartridges 11, 11, . . . , the plurality of the waste liquid vessels 12, 12, . . . , and the plurality of the recovery vessels 13, 13, . . . , is located on the loading base 21. As illustrated also in FIG. 3, the rack 6 comprises a stand 61, a cartridge holder 62, and a vessel holder 63.

The stand 61 is provided with pillar-shaped sections $61a$, $61a$, which are spaced apart from each other. The pillar-shaped sections $61a$, $61a$ of the stand 61 hold the cartridge holder 62 such that the cartridge holder 62 is capable of moving vertically. The stand 61 is also provided with a bottom plate $61b$, on which the pillar-shaped sections $61a$, $61a$ are supported. The region of the bottom plate $61b$, which region is located between the pillar-shaped sections $61a$, $61a$, holds the vessel holder 63 such that the vessel holder 63 is capable of undergoing forward and backward movements.

The cartridge holder 62 has a two-part structure, which is formed with joining of a front plate material and a rear plate material. The cartridge holder 62 comprises a holding section $62a$, which extends horizontally, and support legs $62b$, $62b$, which extend vertically from opposite end regions of the holding section $62a$. Each of the support legs $62b$, $62b$ of the cartridge holder 62 is inserted for vertical movement into one of vertically extending sliding grooves $61c$, $61c$ of the pillar-shaped sections $61a$, $61a$ of the stand 61. The support legs $62b$, $62b$ of the cartridge holder 62 are urged upwardly by urging members (not shown), which are incorporated in the stand 61. The holding section $62a$ of the cartridge holder 62 has a plurality of holding holes $62c$, $62c$, . . . , which stand side by side with one another. Each of the extracting cartridges 11, 11, . . . is inserted from above into one of the holding holes $62c$, $62c$, . . . of the cartridge holder 62, and lower ends of the protrusions $11d$, $11d$ (illustrated in FIG. 10), which are formed on the opposite sides of the side wall of the tubular main body $11a$ of the extracting cartridge 11, are engaged with engagement members (not shown) located in the cartridge holder 62 and are held by the engagement members. The engagement members located in the cartridge holder 62 are capable of being moved. At the time at which the engagement members located in the cartridge holder 62 are moved, the engagement members release the engagement with the protrusions 11d, 11d of each of the extracting cartridges 11, 11, . . . As a result, all of the extracting cartridges 11, 11, . . . are simultaneously allowed to fall down from the cartridge holder 62 and are thus scrapped.

The cartridge holder 62 also has pin receiving holes 62d, 62d, which are formed at opposite areas of the top surface of the cartridge holder 62. In the state in which the extracting cartridges 11, 11, . . . are to be used for the extraction of the nucleic acid, each of bottom ends 49a, 49a of push pins 49, 49 (illustrated in FIG. 1), which act as the position adjusting means as will be described later, engages with one of the pin receiving holes 62d, 62d of the cartridge holder 62 and pushes down the cartridge holder 62. As illustrated in FIG. 3, in the state in which the cartridge holder 62 is located at the raised position, the discharging bottom end 11c of each of the extracting cartridges 11, 11, . . . having been held by the cartridge holder 62 is located at the position more upward than the waste liquid vessels 12, 12, . . . and the recovery vessels 13, 13, . . . having been set on the vessel holder 63. As illustrated in FIG. 4, in the state in which the cartridge holder 62 has been pushed down by the push pins 49, 49 acting as the position adjusting means, the discharging bottom end 11c of each of the extracting cartridges 11, 11, . . . having been held by the cartridge holder 62 is inserted by a predetermined length into the corresponding one of the waste liquid vessels 12, 12, . . . , which have been set on the vessel holder 63, or the corresponding one of the recovery vessels 13, 13, . . . , which have been set on the vessel holder 63.

The vessel holder 63 is provided with a plurality of waste liquid vessel holding holes 63a, 63a, . . . , which stand side by side in a row extending horizontally, and a plurality of recovery vessel holding holes 63b, 63b, . . . , which stand side by side in a row extending horizontally. The row of the waste liquid vessel holding holes 63a, 63a, . . . and the row of the recovery vessel holding holes 63b, 63b, . . . are parallel with each other. The plurality of the waste liquid vessels 12, 12, . . . are held in a row within the waste liquid vessel holding holes 63a, 63a, . . . , respectively, which are located on the rear side. Also, the plurality of the recovery vessels 13, 13, . . . are held in a row within the recovery vessel holding holes 63b, 63b, . . . , respectively, which are located on the front side. The waste liquid vessel holding holes 63a, 63a, . . . are located at the pitches identical with the pitches of the holding holes 62c, 62c, . . . of the cartridge holder 62 and at the positions corresponding to the positions of the holding holes 62c, 62c, . . . of the cartridge holder 62. Also, the recovery vessel holding holes 63b, 63b, . . . are located at the pitches identical with the pitches of the holding holes 62c, 62c, . . . of the cartridge holder 62 and at the positions corresponding to the positions of the holding holes 62c, 62c, . . . of the cartridge holder 62. The vessel holder 63 is thus set such that each of the waste liquid vessels 12, 12, . . . or each of the recovery vessels 13, 13, . . . is located under one of the extracting cartridges 11, 11, . . . having been held by the cartridge holder 62. Such that the waste liquid vessels 12, 12, . . . and the recovery vessels 13, 13, . . . may be discriminated from each other, the sizes, the shapes, or the like, of the waste liquid vessels 12, 12, . . . should preferably be different from the sizes, the shapes, or the like, of the recovery vessels 13, 13, . . .

The vessel holder 63 is urged toward the front side by urging members (not shown), which are incorporated in the stand 61. The movements (i.e., the forward and backward movements) of the vessel holder 63 for the vessel changeover are performed with an actuating member 31 (illustrated in FIG. 2) of the loading base 21. Specifically, the actuating member 31 of the loading base 21 passes through an opening formed in the bottom plate 61b of the stand 61 and engages with an engagement hole (not shown) of the bottom part of the vessel holder 63. Also, the actuating member 31 is moved by a vessel changeover motor (a DC motor) 32 in order to move the vessel holder 63 backwardly. The recovery vessels 13, 13, . . . are thus located at the position under the cartridge holder 62. In the state in which the actuating member 31 is not operated, the vessel holder 63 is urged toward the front side by the urging members (not shown), which are incorporated in the stand 61, such that the waste liquid vessels 12, 12, . . . are located at the position under the cartridge holder 62. The vessel changeover motor 32 is controlled in accordance with results of detection made by position sensors 33a and 33b (illustrated in FIG. 2).

The waste liquid vessel holding holes 63a, 63a, . . . and the recovery vessel holding holes 63b, 63b, . . . are constituted of bottomed holes. Therefore, in cases where a liquid drops into the waste liquid vessel holding holes 63a, 63a, . . . or the recovery vessel holding holes 63b, 63b, . . . in the state in which the waste liquid vessels 12, 12, . . . have not been set in the waste liquid vessel holding holes 63a, 63a, . . . or in which the recovery vessels 13, 13, . . . have not been set in the recovery vessel holding holes 63b, 63b, . . . , the problems are capable of being prevented from occurring in that the liquid flows out to the exterior and contaminates the exterior equipment.

<Pressurized Air Supplying Mechanism>

As illustrated in FIG. 1 and FIG. 2, the pressurized air supplying mechanism 4 comprises a pressurizing head 40, which is capable of moving vertically with respect to the rack 6 of the loading mechanism 3. The pressurized air supplying mechanism 4 also comprises a plurality of (in this example, eight) air nozzles 41, 41, . . . , which are fitted to the pressurizing head 40 and located in a row. As illustrated also in FIG. 5, the pressurized air supplying mechanism 4 further comprises an air pump 43 for producing the pressurized air. The pressurized air supplying mechanism 4 still further comprises a relief valve 44 for releasing the air path to the ambient atmosphere. The pressurized air supplying mechanism 4 also comprises a plurality of on-off valves 45, 45, which are connected respectively to the air nozzles 41, 41, . . . And which independently turn on and off the supply of the pressurized air from the air pump 43. The pressurized air supplying mechanism 4 further comprises a plurality of pressure sensors 46, 46, . . . , which are respectively associated with the air nozzles 41, 41, . . . in order to detect the internal pressures within the extracting cartridges 11, 11, . . . The pressurized air supplying mechanism 4 successively supplies the pressurized air into the extracting cartridges 11, 11, . . .

The pressurizing head 40 is held for vertical movement by guide rods 24, 24, which extend vertically between an intermediate frame 22 and a top frame 23 of the apparatus main body 2. Also, a ball nut 40a secured to the pressurizing head 40 is engaged with a ball screw 25, which extends vertically between the intermediate frame 22 and the top frame 23 of the apparatus main body 2. The ball screw 25 is rotated by a vertical movement motor (a pulse motor) 47 (illustrated in FIG. 2) via a timing belt and a pulley. In accordance with the rotation of the ball screw 25, the pressurizing head 40 is moved vertically. The pressurizing head 40 is moved by being controlled in accordance with the results of detection of photo sensors 48a, 48b, and 48c (illustrated in FIG. 2). The pressurizing head 40 is also provided with the push pins 49, 49, which are located on opposite sides of the pressurizing head 40 and act as the position adjusting means. Each of the push pins 49, 49 is urged by a spring 49b downwardly and is capable of moving vertically. Each of the bottom ends 49a, 49a of the push pins 49, 49 engages with one of the pin receiving holes 62d, 62d, which are formed in the top surface of the cartridge holder 62. The push pins 49, 49 thus adjust the position of the cartridge holder 62 and push down the cartridge holder 62.

The push pins 49, 49 of the pressurizing head 40 are located so as to push the front side positions on the cartridge holder 62, such that the push pins 49, 49 do not interfere with horizontal movements of a washing liquid injecting nozzle 51w and a recovery liquid injecting nozzle 51r, which will be described later, in the state in which the push pins 49, 49 push down the cartridge holder 62.

The air nozzles 41, 41, . . . are fitted for vertical movement to the pressurizing head 40 and are urged downwardly. Also, a sheet-shaped sealing material 42 is located under the air nozzles 41, 41, . . . The sealing material 42 has a plurality of communication holes 42a, 42a, . . . (illustrated in FIG. 2), each of which corresponds to one of the air nozzles 41, 41, . . . At the time at which the pressurizing head 40 is moved down, the bottom end of each of the air nozzles 41, 41, . . . pushes the sealing material 42 against the top end opening of the corresponding extracting cartridge 11 having been set on the cartridge holder 62 and thus closes the top end opening of the corresponding extracting cartridge 11. Each of the air nozzles 41, 41, . . . is thus capable of supplying the pressurized air through the communication hole 42a into the extracting cartridge 11.

Ordinarily, the relief valve 44 is in the off state. In cases where the pressurized air contained in the pressurized air path between the air pump 43 and the on-off valves 45, 45, . . . is to be discharged from the pressurized air path, the relief valve 44 is opened to the ambient atmosphere. The pressurized air circuit is constituted such that each of the on-off valves 45, 45, . . . (in the example shown in FIG. 5, two-way solenoid valves) is turned on selectively in order to introduce the pressurized air from the air pump 43 via the corresponding air nozzle 41 into the corresponding extracting cartridge 11.

Each of the pressure sensors 46, 46, . . . is associated with one of the air nozzles 41, 41, . . . and detects the internal pressure of the corresponding extracting cartridge 11. At the time at which the detected internal pressure of the extracting cartridge 11 becomes equal to a predetermined pressure range (for example 50-200 kPa, and preferably 80-120 kPa) for a pressurization upper limit, the corresponding on-off valve 45 is turned off by a control unit 8 (illustrated in FIG. 6) having received a detection signal from the pressure sensor 46, and the supply of the pressurized air into the extracting cartridge 11 is ceased. Also, in cases where a pressure drop due to completion of the liquid discharging from the extracting cartridge 11 is detected, completion of the pressurization is judged, and the processing advances to the next step.

In FIG. 6, a control system for the pressurized air path with respect to one extracting cartridge 11 is shown. In accordance with outputs from the control unit 8, the turning on and off of the air pump 43 and the turning on and off of each of the on-off valves 45, 45, . . . are performed. The control unit 8 receives a detected pressure signal, which is sent from each of the pressure sensors 46, 46, . . . , an operation signal, which is inputted from an operation panel 7 located at the top of the apparatus main body 2, a sample liquid kind signal, which is sent from an information reading device 9, and the like. The control unit 8 controls the pressurization in accordance with the received signals and a program incorporated in the control unit 8.

With the constitution described above, each of the on-off valves 45, 45, . . . is turned on in order to introduce the pressurized air into the corresponding extracting cartridge 11. At the time at which the internal pressure detected by the corresponding pressure sensor 46 becomes equal to the predetermined pressure range for the pressurization upper limit, the on-off valve 45 is turned off in order to confine the area within the extracting cartridge 11 in the pressurized state. The pressure is thereby exerted upon the sample liquid S, the washing liquid W, or the recovery liquid R, which has been injected into the extracting cartridge 11. The sample liquid S, the washing liquid W, or the recovery liquid R, which has been injected into the extracting cartridge 11, is thereby caused to pass through the filter member 11b of the extracting cartridge 11 under pressure and discharged from the extracting cartridge 11. The point of time of pressurization completion, at which the liquid discharging from the extracting cartridge 11 has been completed, is detected by the corresponding pressure sensor 46 in accordance with the internal pressure drop occurring at the time of the completion of the liquid discharging.

Also, the control unit 8 described above alters the predetermined pressure range for the pressurization upper limit in accordance with the characteristics of the sample liquid S. For example, as will be described later with reference to the flow chart of FIG. 7, firstly, the sample liquid S having been accommodated within each of the extracting cartridges 11, 11, . . . is pressurized under predetermined conditions. The extraction time required for the sample liquid S varies in accordance with the kind of the sample liquid S. In cases where the extraction time required for the sample liquid S is long, the extraction time required at the time of the pressurization of the washing liquid W, which pressurization is performed after the pressurization of the sample liquid S, and the extraction time required at the time of the pressurization of the recovery liquid R, which pressurization is performed after the pressurization of the washing liquid W, are apt to become long. Therefore, such that the processing time may be kept short, in cases where the extraction time required at the time of the pressurization of the sample liquid S is longer by a predetermined length than a reference value, the predetermined pressure range for the pressurization upper limit with respect to the washing liquid W and the predetermined pressure range for the pressurization upper limit with respect to the recovery liquid R are altered to high pressures. Specifically, in accordance with a variation in extraction time required for the sample liquid S, the predetermined pressure range for the pressurization upper limit at the time of the pressurization of the washing liquid W, which pressurization is performed after the pressurization of the sample liquid S, and the predetermined pressure range for the pressurization upper limit at the time of the pressurization of the recovery liquid R, which pressurization is performed after the pressurization of the washing liquid W, are altered. The optimum pressure setting is thus performed in accordance with the kind of the sample liquid S.

Further, in accordance with the operation signal, which is inputted from the operation panel 7, the sample liquid kind signal, which is sent from the information reading device 9, and the like, the control unit 8 alters a mode of control so as to perform the extraction processing with a processing procedure (i.e., a protocol) and setting values, including the predetermined pressure range for the pressurization upper limit, which are optimum for the kind of the sample liquid S. Specifically, in cases where the kind of the sample liquid S to be processed is altered, the control unit 8 alters the mode of pressurization control, the quantity of the processing liquid, and the number of times of the washing operation and adds a step of injecting a reagent, and the like. For example, in cases where information representing the kind of the sample, or the like, is inputted from a keyboard of the operation panel 7, the protocol, the setting values, and the like, which have been programmed previously, are selected for the control. Also, the reagent to be used varies for different kinds of samples to be processed. Information represented by a bar code, an IC chip, or the like, which is appended to the reagent, is read by the information reading device 9, and the protocol, the setting values, and the like, which have been programmed previously, are selected for the control in accordance with the thus read information. Further, information corresponding to the sample liquid S may be read by the information reading device 9 from a storage device, such as a CF card (a memory card), on which the information has been recorded, and the protocol, the setting values, and the like, may be selected for the control in accordance with the thus read information.

During the pressurization processing described above, the introduction of the pressurized air into the plurality of the extracting cartridges 11, 11, . . . is performed by the actuation of the air pump 43 and the turning on and off of the on-off valves 45, 45, . . . , which turning on and off are performed in accordance with the results of the detection made by the pressure sensors 46, 46, . . . The introduction of the pressurized air may be performed successively for each of the extracting cartridges 11, 11, . . . Alternatively, the introduction of the pressurized air may be performed simultaneously for a plurality of the extracting cartridges 11, 11, . . . In cases where the introduction of the pressurized air is to be performed successively for each of the extracting cartridges 11, 11, . . . , one of the on-off valves 45, 45, . . . , which have been in the off state, is turned on in order to introduce the pressurized air into the corresponding extracting cartridge 11 and is then turned off in accordance with the result of the detection made by the corresponding pressure sensor 46. Thereafter, the next on-off valve 45 is turned on in order to introduce the pressurized air into the corresponding extracting cartridge 11 and is then turned off in accordance with the result of the detection made by the corresponding pressure sensor 46. The operation described above is iterated, and the pressurized air is thus successively introduced into the plurality of the extracting cartridges 11, 11, . . . The flow chart of FIG. 7 shows the operations performed in the manner described above.

In cases where the introduction of the pressurized air is to be performed simultaneously for a plurality of the extracting cartridges 11, 11, . . . , a plurality of the on-off valves 45, 45, . . . among all of the on-off valves 45, 45, . . . , which have been in the off state, are turned on in order to introduce the pressurized air simultaneously into the corresponding extracting cartridges 11, 11, . . . and are then turned off in accordance with the results of the detection made by the corresponding pressure sensors 46, 46, . . . In cases where the introduction of the pressurized air is thus performed simultaneously for the plurality of the extracting cartridges 11, 11, . . . , the delivery quantity of the air pump 43 is controlled in accordance with the number of the on-off valves 45, 45, . . . to be turned on, and the pressure increase rate is set at a predetermined rate. The control of the delivery quantity of the air pump 43 may be performed with, for example, PWM control. Specifically, with respect to the voltage applied to the air pump 43, time ratio variation control (i.e., on-off duty control) is performed in accordance with the number of the extracting cartridges 11, 11, . . . , such that the number of revolutions of the air pump 43 is set to be large for a large number of the extracting cartridges 11, 11, . . . In this manner, the pressure increase rate of the pressurized air introduced into the extracting cartridges 11, 11, . . . is kept uniform, and the pressure, which is confined within each of the extracting cartridges 11, 11, . . . when the corresponding on-off valve 45 is turned off in accordance with the result of detection of the predetermined pressure range for the pressurization upper limit made by the corresponding pressure sensor 46, is kept at a predetermined pressure.

Also, in accordance with a variation in pressure within each of the extracting cartridges 11, 11, . . . , which pressure is detected by the corresponding pressure sensor 46, detection is made as to whether the extracting cartridge 11 has been or has not been set in the cartridge holder 62, whether the sample liquids, the washing liquid W, or the recovery liquid R has been or has not been injected into the extracting cartridge 11, whether the quantity of the liquid having been injected into the extracting cartridge 11 is or is not sufficient, and whether the clogging of the filter member 11b has or has not occurred. The variation in pressure within each of the extracting cartridges 11, 11, . . . will be described later with reference to FIG. 8.

The operation of the relief valve 44 illustrated in FIG. 5 for releasing the air path to the ambient atmosphere is performed at the same time as the turning-on operation of the on-off valve 45, which turning-on operation is performed in accordance with the detection of the completion of the liquid discharging from the corresponding extracting cartridge 11. The pressurized air remaining within the extracting cartridge 11 is thus discharged, and the problems are prevented from occurring in that liquid scattering occurs due to air jetting from the discharging bottom end 11c of the extracting cartridge 11.

Alternatively, the operation of the relief valve 44 illustrated in FIG. 5 for releasing the air path to the ambient atmosphere may be performed when all of the on-off valves 45, 45, . . . are in the off state. Excessive pressurized air due to the continuous operation of the air pump 43 is thus discharged through the relief valve 44, and the problems are thus prevented from occurring in that the pressurized air having an increased pressure due to the continuous operation of the air pump 43 is supplied into the extracting cartridge 11 at the time at which the corresponding on-off valve 45 is turned on. As another alternative, the operation of the relief valve 44 illustrated in FIG. 5 for releasing the air path to the ambient atmosphere may be performed both at the same time as the turning-on operation of the on-off valve 45, which turning-on operation is performed in accordance with the detection of the completion of the liquid discharging from the corresponding extracting cartridge 11, and at the time at which all of the on-off valves 45, 45, . . . are in the off state as described above.

In the descriptions of the embodiments, the air pump is a diaphragm pump. However, other kinds of pumps such as a plunger pump and a syring pump, which can function as a pressurized air source, may be used as the air pump.

<Liquid Injecting Mechanism>

The liquid injecting mechanism 5 comprises the washing liquid injecting nozzle 51w and the recovery liquid injecting nozzle 51r, which are secured to a nozzle moving base 50 capable of moving horizontally. The liquid injecting mechanism 5 also comprises a washing liquid supplying pump 52w (illustrated in FIG. 2) for supplying the washing liquid W, which has been accommodated in a washing liquid bottle 56*w*, into the washing liquid injecting nozzle 51*w*. The liquid injecting mechanism 5 further comprises a recovery liquid supplying pump 52*r* (illustrated in FIG. 2) for supplying the recovery liquid R, which has been accommodated in a recovery liquid bottle 56*r*, into the recovery liquid injecting nozzle 51*r*. The liquid injecting mechanism 5 still further comprises a waste liquid bottle 57, which is located on the loading base 21.

The nozzle moving base 50 is held for horizontal movement by a guide rail 27, which extends horizontally and is secured to a vertical wall 26 of the apparatus main body 2. The horizontal movement of the nozzle moving base 50 is ceased successively above the extracting cartridges 11, 11, . . . by a nozzle moving motor (not shown) constituted of a pulse motor. In a state of restoration of the nozzle moving base 50, the nozzle moving base 50 is stopped at the position above the waste liquid bottle 57. An end of the washing liquid injecting nozzle 51*w* and an end of the recovery liquid injecting nozzle 51*r* are bent downwardly. The washing liquid injecting nozzle 51*w* is connected to the washing liquid supplying pump 52*w* via a changeover valve 55*w* (illustrated in FIG. 2). The washing liquid supplying pump 52*w* is connected to the washing liquid bottle 56*w* via the changeover valve 55*w*. Also, the recovery liquid injecting nozzle 51*r* is connected to the recovery liquid supplying pump 52*r* via a changeover valve 55*r*. The recovery liquid supplying pump 52*r* is connected to the recovery liquid bottle 56*r* via the changeover valve 55*r*. The washing liquid bottle 56*w* and the recovery liquid bottle 56*r* are fitted to a side of the apparatus main body 2. Each of the washing liquid supplying pump 52*w* and the recovery liquid supplying pump 52*r* is constituted of a syringe pump. A piston member of the washing liquid supplying pump 52*w* is actuated by a pump motor 53*w* (illustrated in FIG. 2), which is constituted of a pulse motor, and in accordance with a result of a position detection made by a sensor 54*w* in order to inject a predetermined quantity of the washing liquid W. Also, a piston member of the recovery liquid supplying pump 52*r* is actuated by a pump motor 53*r* (illustrated in FIG. 2), which is constituted of a pulse motor, and in accordance with a result of a position detection made by a sensor 54*r* in order to inject a predetermined quantity of the recovery liquid R.

Specifically, in cases where the washing liquid W is to be injected, the changeover valve 55*w* is changed over to the side for the washing liquid bottle 56*w*. Also, the pump motor 53*w* is actuated in order to retreat the piston member of the washing liquid supplying pump 52*w*, and the washing liquid W is thus sucked into the washing liquid supplying pump 52*w*. Thereafter, the changeover valve 55*w* is changed over to the side for the washing liquid injecting nozzle 51*w*. Also, the pump motor 53*w* is actuated in order to advance the piston member of the washing liquid supplying pump 52*w*, and the washing liquid W is thus discharged from the washing liquid injecting nozzle 51*w* into the waste liquid bottle 57 until air contained in the washing liquid path has been discharged. The actuation of the washing liquid supplying pump 52*w* is then ceased. Thereafter, the washing liquid injecting nozzle 51*w* is moved to the position above one of the extracting cartridges 11, 11, . . . The actuation quantity of the washing liquid supplying pump 52*w* is then controlled, and the predetermined quantity of the washing liquid W is injected into the extracting cartridge 11.

In cases where the recovery liquid R is to be injected, the changeover valve 55*r* is changed over to the side for the recovery liquid bottle 56*r*. Also, the pump motor 53*r* is actuated in order to retreat the piston member of the recovery liquid supplying pump 52*r*, and the recovery liquid R is thus sucked into the recovery liquid supplying pump 52*r*. Thereafter, the changeover valve 55*r* is changed over to the side for the recovery liquid injecting nozzle 51*r*. Also, the pump motor 53*r* is actuated in order to advance the piston member of the recovery liquid supplying pump 52*r*, and the recovery liquid R is thus discharged from the recovery liquid injecting nozzle 51*r* into the waste liquid bottle 57 until air contained in the recovery liquid path has been discharged. The actuation of the recovery liquid supplying pump 52*r* is then ceased. Thereafter, the recovery liquid injecting nozzle 51*r* is moved to the position above one of the extracting cartridges 11, 11, . . . The actuation quantity of the recovery liquid supplying pump 52*r* is then controlled, and the predetermined quantity of the recovery liquid R is injected into the extracting cartridge 11.

Besides the control of the pressurization, the control unit 8 (illustrated in FIG. 6) described above also controls the operations of the loading mechanism 3, the pressurized air supplying mechanism 4, and the liquid injecting mechanism 5. In accordance with the input operation performed from the operation panel 7 located at the top of the apparatus main body 2, the control unit 8 controls so as to perform the series of the automatic extracting operation in accordance with the program incorporated in the control unit 8.

The extracting operation performed with the nucleic acid extracting apparatus 1 described above will hereinbelow be described in detail.

Firstly, the extracting cartridges 11, 11, . . . are set in the cartridge holder 62 of the rack 6 of the loading mechanism 3. Also, the waste liquid vessels 12, 12, . . . and the recovery vessels 13, 13, . . . are set in the vessel holder 63 of the rack 6 of the loading mechanism 3. The rack 6 is then located on the loading base 21 of the apparatus main body 2. Thereafter, the sample liquid S, which has been subjected to the dissolution processing, is introduced with a pipette, or the like, successively into each of the extracting cartridges 11, 11, . . . Alternatively, before the rack 6 is loaded on the nucleic acid extracting apparatus 1, the sample liquid S may be introduced into each of the extracting cartridges 11, 11, . . . having been set in the rack 6. As another alternative, before the extracting cartridges 11, 11, . . . are set in the rack 6, the sample liquid S may be introduced into each of the extracting cartridges 11, 11, . . .

Thereafter, the nucleic acid extracting apparatus 1 is actuated with an operation from the operation panel 7. The pressurizing head 40 of the pressurized air supplying mechanism 4 is moved downwardly by the vertical movement motor 47 of the pressurized air supplying mechanism 4, and the bottom ends 49*a*, 49*a* of the push pins 49, 49 engage with the pin receiving holes 62*d*, 62*d* of the cartridge holder 62. The push pins 49, 49 thus push down the cartridge holder 62 and adjust the position of the cartridge holder 62. Also, as illustrated in FIG. 4, the push pins 49, 49 cause the discharging bottom end 11*c* of each of the extracting cartridges 11, 11, . . . to be inserted by the predetermined length into the corresponding waste liquid vessel 12, such that the liquid discharged from the extracting cartridge 11 may not leak to the exterior due to scattering, or the like. The pressurizing head 40 is moved downwardly even further. As a result, the bottom end of each of the air nozzles 41, 41, . . . pushes the sealing material 42 against the top end opening of the corresponding extracting cartridge 11 and thus closes the top end opening of the corresponding extracting cartridge 11. Since the push pins 49, 49 adjust the position of the cartridge holder 62, each of the air nozzles 41, 41, . . . is capable of accurately coming into close contact with the top end opening of the corresponding extracting cartridge 11 and is thus capable of reliably closing the top end opening of the corresponding extracting cartridge 11.

Thereafter, the operation for supplying the pressurized air is performed. An example of how the pressurization control is performed will be described hereinbelow with reference to FIG. 7. As illustrated in FIG. 7, in a step S1, information representing an upper limit pressure Pa (i.e., the predetermined pressure for the pressurization upper limit) is read. At the initial stage, the upper limit pressure Pa is set at the reference value. Also, in a step S2, the first on-off valve 45 is turned on, and the air pump 43 is actuated. As a result, the pressurized air is supplied from the air pump 43 through the first air nozzle 41 into the first extracting cartridge 11. In a step S3, a pressure "p" in the first extracting cartridge 11 is detected by the first pressure sensor 46. Further, in a step S4, a judgment is made as to whether the pressure "p" having been detected has or has not become equal to the upper limit pressure Pa.

In cases where it has been detected in the step S4 that the pressure "p" having been supplied into the extracting cartridge 11 has become equal to the upper limit pressure Pa, in a step S5, the first on-off valve 45 is turned off in order to confine the area within the first extracting cartridge 11 in the pressurized state. Thereafter, in a step S6, the second on-off valve 45 is turned on, and the pressurized air is supplied through the second air nozzle 41 into the second extracting cartridge 11. The operations described above are iterated successively, and the pressure is applied to all of the extracting cartridges 11, 11, . . . Further, in a step S7, the air pump 43 is turned off. In each of the extracting cartridges 11, 11, . . . into which the pressurized air has been introduced, the sample liquid S is caused to pass through the filter member 11b of the extracting cartridge 11 under pressure, and the nucleic acid contained in the sample liquid S is adsorbed to the filter member 11b. The other liquid constituents of the sample liquid S are discharged through the discharging bottom end 11c of the extracting cartridge 11 into the waste liquid vessel 12.

Thereafter, in a step S8, a judgment is made as to whether the liquid discharging has or has not been completed. Specifically, in each of the extracting cartridges 11, 11, . . . , at the time at which all of the sample liquid S having been introduced into the extracting cartridge 11 has passed through the filter member 11b, and the liquid discharging has thus been completed, the internal pressure "p" in the extracting cartridge 11 drops markedly. The judgment as to whether the liquid discharging has or has not been completed is made in accordance with the drop of the internal pressure "p" in the extracting cartridge 11. In cases where it has been judged in the step S8 that the liquid discharging from the first extracting cartridge 11 has been completed, in a step S9, a judgment is made as to whether an extraction time (i.e., a pressurization time) tn, which has occurred between the start of the pressurization and the completion of the liquid discharging, is or is not longer than a predetermined value (an upper limit) T. In cases where it has been judged in the step S9 that the extraction time tn is longer than the predetermined value T, in a step S10, a value of Δp is added to the aforesaid upper limit pressure Pa, and information representing the resulting upper limit pressure Pa is stored in a memory.

At the time at which the completion of the liquid discharging has been detected by the pressure sensors 46, 46, . . . with respect to all of the extracting cartridges 11, . . . , the pressurization processing is finished, and the pressurizing head 40 is moved upwardly.

The processing of the step S9 and the processing of the step S10 are performed for each of the extracting cartridges 11, 11, . . . As for the extracting cartridge 11, in which the extraction time tn required for the sample liquid S was long, in each of the pressurization processing for the washing liquid W and the pressurization processing for the recovery liquid R, which are performed thereafter, the information representing the upper limit pressure Pa having been corrected in the manner described above is read in the step S1, and the pressure of the pressurized air applied into the extracting cartridge 11 is thus set to be high in order to promote the liquid discharging, and the processing time is thereby kept short.

In the pressurization control described above, the relief valve 44 is operated in the manner described below. Specifically, during the supply of the pressurized air described above, the first on-off valve 45 is turned on, and the air pump 43 is actuated while the on-off valves 45, 45, . . . other than the first on-off valve 45 are in the off state. The pressurized air is thus supplied from the air pump 43 through the first air nozzle 41 into the first extracting cartridge 11. At the time at which it has been detected by the corresponding pressure sensor 46 that the pressure within the first extracting cartridge 11 has become equal to the predetermined pressure range for the pressurization upper limit, the first on-off valve 45 is turned off in order to confine the area within the first extracting cartridge 11 in the pressurized state, and the relief valve 44 is opened. At the time at which the second on-off valve 45 is then turned on, the relief valve 44 is closed, and the pressurized air is supplied through the second air nozzle 41 into the second extracting cartridge 11. The operations described above are iterated successively, and the areas within all of the extracting cartridges 11, 11, . . . are pressurized. Also, at the time at which the supply of the pressurized air into all of the extracting cartridges 11, 11, . . . has been finished, and all of the on-off valves 45, 45, . . . have been set in the off state, the actuation of the air pump 43 is ceased, and the relief valve 44 is opened in order to release the air path to the ambient atmosphere.

Further, when all of the sample liquid S having been introduced into the extracting cartridge 11 has passed through the filter member 11b of the extracting cartridge 11, and the liquid discharging has thus been completed, the internal pressure within the extracting cartridge 11 drops markedly. At the time at which the pressure drop is detected by the corresponding pressure sensor 46, the corresponding on-off valve 45 is turned on, and the pressurized air, which remains within the extracting cartridge 11, is released through the relief valve 44 to the ambient atmosphere. The problems are thus prevented from occurring in that the pressurized air, which remains within the extracting cartridge 11, is jetted out together with the liquid from the discharging bottom end 11c of the extracting cartridge 11.

In the normal operation state, the internal pressure, which is formed by the introduction of the pressurized air into the extracting cartridge 11, varies in accordance with characteristics indicated by a curve A in FIG. 8. In FIG. 8, a curve B is a differentiation wave form representing the quantity of the variation in internal pressure. As indicated by the curve A, the internal pressure increases linearly from a point of time 0, at which the on-off valve 45 is turned on in order to begin the introduction of the pressurized air into the extracting cartridge 11. At a point "a" at which the internal pressure has become equal to the predetermined pressure Pa (for example 50-200 kPa, and preferably 80-120 kPa) for the pressurization upper limit, the on-off valve 45 is turned off in order to confine the area within the extracting cartridge 11 in the pressurized state. The internal pressure is exerted upon the liquid and causes the liquid to pass through the filter member 11b of the extracting cartridge 11. The liquid quantity in the extracting cartridge 11 decreases little by little, and the internal pressure drops little by little. At a point "b," all of the liquid having been introduced into the extracting cartridge 11 has passed through the filter member 11b of the extracting cartridge 11, and the liquid discharging is completed. At the point "b," air resistance at the filter member 11b decreases, and the internal pressure drops markedly. In the differentiation wave form curve B, the variation in pressure at the point "b" occurs markedly. Therefore, the variation in pressure at the point "b" is detected, and the completion of the pressurization is judged in accordance with the detected variation in pressure at the point "b."

Alternatively, the judgment of the completion of the pressurization may be made by detecting that the quantity of the variation in pressure drop per unit time has become equal to at least a predetermined value. As another alternative, the judgment of the completion of the pressurization may be made by detecting that the detected pressure has become equal to at most a predetermined pressure range for the pressurization completion judgment. The aforesaid techniques for making the judgment of the completion of the pressurization should preferably be utilized in combination, such that the time required for making the judgment may be kept short.

In the cases of the pressurization of the sample liquid S, the variation in pressure occurs in a different manner in accordance with the viscosity of the sample liquid S, or the like. As for a sample liquid S having a low viscosity, the degree of the pressure drop from the point "a" to the point "b" becomes large, and the time occurring between the point "a" and the point "b" becomes short. Also, in cases where the viscosity of the sample liquid S is large, and slight clogging occurs with the filter member 11b, the degree of the pressure drop from the point "a" to the point "b" becomes small, and the time occurring between the point "a" and the point "b" becomes long.

Further, in accordance with the characteristics of the variation in internal pressure within each of the extracting cartridges 11, 11, . . . , which internal pressure is detected by the corresponding pressure sensor 46, a pressurization failure state is detected. For example, the detection is thus made as to whether the extracting cartridge 11 has been or has not been set in the cartridge holder 62, whether the sample liquid S, the washing liquid W, or the recovery liquid R has been or has not been injected into the extracting cartridge 11, whether the area within the extracting cartridge 11 has or has not been confined appropriately, whether the quantity of the liquid having been injected into the extracting cartridge 11 is or is not sufficient, and whether the clogging of the filter member 11b has or has not occurred.

The detection of the pressurization failure state is made in cases where, when a predetermined length of time has elapsed after the on-off valve 45 is turned on in order to jet out the pressurized air from the air nozzle 41, the pressure detected by the pressure sensor 46 is within a predetermined pressure range for judgment, which is set at a lower level such as 10 kPa or lower, and does not become higher than that level. The state described above is an abnormal state, in which the air resistance is low. Specifically, the state described above is capable of being judged as being the state in which the extracting cartridge 11 has not been set in the cartridge holder 62, the state in which the sample liquid S has not been introduced into the extracting cartridge 11, or the state in which the area between the air nozzle 41 and the extracting cartridge 11 has not been confined appropriately.

In cases where the quantity of the sample liquid S having been injected into the extracting cartridge 11 is smaller than a predetermined quantity, the initial pressure confined within the extracting cartridge 11 becomes higher than the predetermined pressure range for the pressurization failure judgment and is lower than the predetermined pressure range Pa for the pressurization upper limit for the turning off of the on-off valve 45. Also, the liquid discharging from the extracting cartridge 11 is completed in this state, and the pressure drops markedly. In such cases, the state is judged as being the liquid quantity deficiency state, in which the liquid injection quantity is smaller than the predetermined quantity.

In cases where the filter clogging occurs, the detected pressure drops little by little in accordance with the liquid discharging. However, the pressure drop is small. Also, the aforesaid judgment of the completion of the pressurization is not capable of being made when a predetermined length of time has elapsed, and the internal pressure within the extracting cartridge 11 does not become lower than the predetermined pressure range for the pressurization completion judgment. In such cases, it is judged that the filter clogging has occurred. Alternatively, in cases where the time, during which the quantity of the variation in pressure drop per unit time does not become equal to at least the predetermined value, continues for at least a predetermined length of time, it may be judged that the filter clogging has occurred.

The detection of the pressurization failure at the time of the insufficient increase in pressure during the pressurization, the detection of the completion of the pressurization, accompanying the completion of the liquid discharging, and the detection of the filter clogging described above are also performed in the same manner in the washing processing and the recovery processing, which will be described below.

Thereafter, the washing processing is performed. Specifically, after the supply of the pressurized air, the pressurizing head 40 is moved upwardly as described above, and the air nozzles 41, 41, . . . move away from the extracting cartridges 11, 11, . . . When the pressurizing head 40 has been moved up to a height position at which the pressurizing head 40 allows the horizontal movement of the nozzle moving base 50, the upward movement of the pressurizing head 40 is ceased. The washing processing is performed in the state illustrated in FIG. 4, in which the push pins 49, 49 push down the cartridge holder 62 and in which the discharging bottom end 11c of each of the extracting cartridges 11, 11, . . . has been inserted into the corresponding waste liquid vessel 12. More specifically, the nozzle moving base 50 is moved horizontally, and the washing liquid injecting nozzle 51w is stopped at the position above the first extracting cartridge 11. In this state, a predetermined quantity of the washing liquid W is injected from the washing liquid injecting nozzle 51w into the first extracting cartridge 11. The nozzle moving base 50 is then moved successively to the positions above the other extracting cartridges 11, 11, . . . , and the injection of the washing liquid W from the washing liquid injecting nozzle 51w into the extracting cartridges 11, 11, . . . is performed successively. When the injection of the washing liquid W has been finished for all of the extracting cartridges 11, 11, . . . , the pressurizing head 40 is moved downwardly, and the bottom end of each of the air nozzles 41, 41, . . . pushes the sealing material 42 against the top end opening of the corresponding extracting cartridge 11 and thus closes the top end opening of the corresponding extracting cartridge 11. Thereafter, in the same manner as that described above, the on-off valves 45, 45, . . . are turned on successively, and the pressurized air is supplied into the extracting cartridges 11, 11, . . . When the washing liquid W is thus subjected to the pressure, the washing liquid W is caused to pass through the filter member 11b of each of the extracting cartridges 11, 11, . . . , and the impurities other than the nucleic acid are washed off by the washing liquid W. The washing liquid W having passed through the filter member 11b is discharged through the discharging bottom end 11c of the extracting cartridge 11 into the corresponding waste liquid vessel 12. At the time at which all washing liquid W contained in all of the extracting cartridges 11, 11, . . . has passed through the filter members 11b, 11b, . . . of the extracting cartridges 11, 11, . . . and has thus been discharged from the extracting cartridges 11, 11, the pressurizing head 40 is moved upwardly to the initial position. In cases where the washing processing is to be performed a plurality of times, the operation described above is iterated.

In the cases of the washing processing and the recovery processing, which will be described later, the supply of the pressurized air may be performed with respect to a plurality of the extracting cartridges 11, 11, . . . at the same time. Specifically, with respect to all of the extracting cartridges 11, 11, . . . in the normal operating state, which are other than the extracting cartridges 11, 11, . . . having been judged as being in the pressurization failure state or the filter clogging state, the corresponding on-off valves 45, 45, . . . may be turned on at the same time in order to introduce the pressurized air from the air pump 43, which is actuated in a variable mode through the PWM control, into the extracting cartridges 11, 11, . . . which are in the normal operating state. Also, at the time at which the pressurization upper limit pressure is detected by each of the corresponding pressure sensors 46, 46, . . . , the corresponding on-off valve 45 may be turned off.

Further, the operation may be controlled such that, with respect to the extracting cartridges 11, 11, . . . having been judged as being in the pressurization failure state or the filter clogging state, the injection of the washing liquid W and the supply of the pressurized air are not performed.

Thereafter, the recovery processing is performed. Specifically, firstly, in accordance with the upward movement of the pressurizing head 40 performed after the washing processing, the push pins 49, 49 move upwardly, and the cartridge holder 62 of the rack 6 also moves upwardly. The discharging bottom end 11c of each of the extracting cartridges 11, 11, . . . is thus moved upwardly from the corresponding waste liquid vessel 12. Thereafter, the actuating member 31 of the loading mechanism 3 is operated in order to retreat the vessel holder 63. The recovery vessels 13, 13, . . . are thus located under the extracting cartridges 11, 11, . . . The vessel changeover is performed in this manner.

Thereafter, the pressurizing head 40 is moved downwardly, and the bottom ends 49a, 49a of the push pins 49, 49 engage with the pin receiving holes 62d, 62d of the cartridge holder 62. The push pins 49, 49 thus push down the cartridge holder 62. Also, the nozzle moving base 50 is moved horizontally, and the recovery liquid injecting nozzle 51r is stopped at the position above the first extracting cartridge 11. In this state, a predetermined quantity of the recovery liquid R is injected from the recovery liquid injecting nozzle 51r into the first extracting cartridge 11. The nozzle moving base 50 is then moved successively to the positions above the other extracting cartridges 11, 11, . . . , and the injection of the recovery liquid R from the recovery liquid injecting nozzle 51r into the extracting cartridges 11, 11, . . . is performed successively. When the injection of the recovery liquid R has been finished for all of the extracting cartridges 11, 11, . . . , the pressurizing head 40 is moved downwardly even further in the same manner as that described above, and the bottom end of each of the air nozzles 41, 41, . . . pushes the sealing material 42 against the top end opening of the corresponding extracting cartridge 11 and thus closes the top end opening of the corresponding extracting cartridge 11. Thereafter, the on-off valves 45, 45, . . . are turned on successively, and the pressurized air is supplied into the extracting cartridges 11, 11, . . . When the recovery liquid R is thus subjected to the pressure, the recovery liquid R is caused to pass through the filter member 11b of each of the extracting cartridges 11, 11, . . . , and the nucleic acid having been adsorbed to the filter member 11b is separated by the recovery liquid R from the filter member 11b. The nucleic acid having thus been separated from the filter member 11b is discharged together with the recovery liquid R through the discharging bottom end 11c of the extracting cartridge 11 into the corresponding recovery vessel 13. At the time at which all recovery liquid R contained in all of the extracting cartridges 11, 11, . . . has thus been discharged from the extracting cartridges 11, 11, . . . , the pressurizing head 40 is moved upwardly. At this stage, the series of the operations are finished.

The rack 6, for which the extracting operation has been finished, is unloaded from the loading base 21. Also, the extracting cartridges 11, 11, . . . and the waste liquid vessels 12, 12, . . . are taken out respectively from the cartridge holder 62 and the vessel holder 63 and scrapped. The recovery vessels 13, 13, . . . are taken out from the vessel holder 63. When necessary, the recovery vessels 13, 13, . . . are closed with covers. Thereafter, the recovery vessels 13, 13, . . . are subjected to next nucleic acid analyzing processing, or the like.

In the embodiment described above, the plurality of the extracting cartridges 11, 11, . . . are loaded. However, the nucleic acid extracting apparatus in accordance with the present invention is not limited to the use of the plurality of the extracting cartridges 11, 11, . . . and is applicable also in cases where only one extracting cartridge 11 is used.

In the present embodiment, the washing processing is performed by use of the washing liquid W. However, the washing processing is not always required depending on the filtering performance of the filter member 11b.

Further, in the embodiment as described above, the nucleic acid extracting apparatus is described. However, the present invention is not limited to the nucleic acid extracting apparatus. The present invention may also be adopted to a method for filtering various kinds of predetermined substance through contact with the filter member. Further, it is not necessary to recover the recovery liquid. The predetermined substance can be kept in contact with the filter member during analysis. A liquid for analyzing the reaction color may also be added.

What is claimed is:

1. A nucleic acid extracting apparatus comprising:
a plurality of extracting cartridges each having a filter for adsorbing a predetermined substance in a liquid which is injected into the extracting cartridges, respectively;
a rack for holding the extracting cartridges;
a pressurized air introducing mechanism for introducing pressurized air into the extracting cartridges, wherein the pressurized air introducing mechanism is capable of moving vertically with respect to the rack, the pressurized air introducing mechanism including:

a) an air pump for pressurizing air,
b) on-off valves connected to the air pump for turning on and off the introduction of the pressurized air into each of the extracting cartridges, individually, and
c) pressure sensors for detecting an internal pressure within each of the extracting cartridge, respectively, wherein the pressure sensors and the on-off valves correspond to each other in a one-to-one relationship in order to control each of the corresponding extracting cartridges, respectively; and a control unit for controlling the pressurized air introducing mechanism, wherein the control unit turns on at least one of the on-off valves in order to introduce the pressurized air into at least one of the extracting cartridges corresponding with the at least one on-off valve in accordance with a result of the detection made by at least one of the pressure sensors corresponding with the at least one on-off valve, and when the internal pressure detected by at least one of pressure sensors for the at least one extracting cartridge has become equal to a predetermined pressure range for a pressurization upper limit, the control unit turns off the at least one on-off valve in order to confine the area within the at least one extracting cartridge in the pressurized state, the pressure being thereby exerted upon the liquid having been injected into the at least one extracting cartridge.

2. An apparatus as defined in claim 1 wherein the predetermined pressure range for the pressurization upper limit depends upon the characteristics of the liquid.

3. An apparatus as defined in claim 2 wherein a judgment is made as to whether the internal pressure is within a predetermined pressure range when a predetermined length of time has elapsed after the at least one on-off valve was turned on in order to begin the supply of the pressurized air into the at least one extracting cartridge.

4. An apparatus as defined in claim 2 wherein
at the time at which a pressure drop accompanying completion of the liquid discharging from the at least one extracting cartridge is detected by the at least one pressure sensor, the control unit determines that the pressurization has been completed.

5. An apparatus as defined in claim 2 wherein a state, in which the internal pressure confined within the at least one extracting cartridge is equal to at least a predetermined pressure range for filter clogging detection when a predetermined length of time has elapsed, is judged as being a state in which filter clogging has occurred.

6. An apparatus as defined in claim 2 wherein a state, in which the internal pressure confined within the at least one extracting cartridge is higher than a predetermined pressure range and is lower than the predetermined pressure range for the pressurization upper limit for the turning off of the at least one on-off valve, and liquid discharging from the at least one extracting cartridge is completed in this state, is judged as being a liquid quantity deficiency state, in which the liquid injection quantity is smaller than a predetermined value.

7. An apparatus as defined in claim 1, further comprising a an operation panel for inputting information into the nucleic acid extracting apparatus, wherein said inputted information corresponds to the kind of the liquid accommodated in the at least one extracting cartridge, and the control unit alters an extraction processing procedure and setting values, including the predetermined pressure range for the pressurization upper limit, in accordance with the inputted information.

8. An apparatus as defined in claim 7 wherein a judgment is made as to whether the internal pressure is within a predetermined pressure range when a predetermined length of time has elapsed after the at least one on-off valve was turned on in order to begin the supply of the pressurized air into the at least one extracting cartridge.

9. An apparatus as defined in claim 7 wherein
at the time at which a pressure drop accompanying completion of the liquid discharging from the at least one extracting cartridge is detected by the at least one pressure sensor, the control unit determines that the pressurization has been completed.

10. An apparatus as defined in claim 7 wherein a state, in which the internal pressure confined within the at least one extracting cartridge is equal to at least a predetermined pressure range for filter clogging detection when a predetermined length of time has elapsed, is judged as being a state in which filter clogging has occurred.

11. An apparatus as defined in claim 7 wherein a state, in which the internal pressure confined within the at least one extracting cartridge is higher than the predetermined pressure range and is lower than the predetermined pressure range for the pressurization upper limit for the turning off of the at least one on-off valve, and liquid discharging from the at least one extracting cartridge is completed in this state, is judged as being a liquid quantity deficiency state, in which the liquid injection quantity is smaller than a predetermined value.

12. An apparatus as defined in claim 1 wherein a judgment is made as to whether the internal pressure is within a predetermined pressure range when a predetermined length of time has elapsed after the at least one on-off valve was turned on in order to begin the supply of the pressurized air into the at least one extracting cartridge.

13. An apparatus as defined in claim 1 wherein
at the time at which a pressure drop accompanying completion of the liquid discharging from the at least one extracting cartridge is detected by the at least one pressure sensor, the control unit determines that the pressurization has been completed.

14. An apparatus as defined in claim 1 wherein a state, in which the internal pressure confined within the at least one extracting cartridge is equal to at least a predetermined pressure range for filter clogging detection when a predetermined length of time has elapsed, is judged as being a state in which filter clogging has occurred.

15. An apparatus as defined in claim 1 wherein a state, in which the internal pressure confined within the at least one extracting cartridge is higher than a predetermined pressure range and is lower than the predetermined pressure range for the pressurization upper limit for the turning off of the at least one on-off valve, and liquid discharging from the at least one extracting cartridge is completed in this state, is judged as being a liquid quantity deficiency state, in which the liquid injection quantity is smaller than a predetermined value.

* * * * *